US012683011B2

(12) United States Patent
Galeotti et al.

(10) Patent No.: US 12,683,011 B2
(45) Date of Patent: Jul. 14, 2026

(54) SYSTEM, METHOD, AND COMPUTER PROGRAM PRODUCT FOR SEGMENTING AN IMAGE

(71) Applicant: Carnegie Mellon University, Pittsburgh, PA (US)

(72) Inventors: John Michael Galeotti, Pittsburgh, PA (US); Ling Yu Hung, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 346 days.

(21) Appl. No.: 18/284,165

(22) PCT Filed: Mar. 28, 2022

(86) PCT No.: PCT/US2022/022094
§ 371 (c)(1),
(2) Date: Sep. 26, 2023

(87) PCT Pub. No.: WO2022/204585
PCT Pub. Date: Sep. 29, 2022

(65) Prior Publication Data
US 2024/0177833 A1      May 30, 2024

Related U.S. Application Data

(60) Provisional application No. 63/166,300, filed on Mar. 26, 2021.

(51) Int. Cl.
*G16H 30/40* (2018.01)
*G06T 7/10* (2017.01)
*G06V 10/762* (2022.01)

(52) U.S. Cl.
CPC .............. *G16H 30/40* (2018.01); *G06T 7/10* (2017.01); *G06V 10/762* (2022.01); *G06T 2207/20081* (2013.01)

(58) Field of Classification Search
None
See application file for complete search history.

(56) References Cited

U.S. PATENT DOCUMENTS

| | | | |
|---|---|---|---|
| 2008/0103996 A1* | 5/2008 | Forman ................. | G06N 20/00 706/12 |
| 2008/0174593 A1* | 7/2008 | Ham ................... | G06F 16/9574 345/418 |

(Continued)

OTHER PUBLICATIONS

Daoud et al., "Reliable and accurate needle localization in curvilinear ultrasound images using signature-based analysis of ultrasound beamformed radio frequency signals," Med. Phys. 47(6), Jun. 2020 (Year: 2020).*

(Continued)

*Primary Examiner* — Soo Shin
(74) *Attorney, Agent, or Firm* — The Webb Law Firm

(57) ABSTRACT

Provided are systems, methods, and computer program products for segmenting an image. A method includes segmenting each image in a sequence of images including a needle into a needle and at least one needle artifact based on processing each image with a first machine-learning model trained with a plurality of hard labels for a plurality of images, resulting in a plurality of hard-labeled images, transforming each hard-labeled image of the plurality of hard-labeled images into a soft-labeled image including pixel values corresponding to an effect of the at least one needle artifact, resulting in a plurality of soft-labeled images, and segmenting at least one image of the sequence of images based on processing the at least one image with a second machine-learning model trained at least partially with the plurality of soft-labeled images.

21 Claims, 9 Drawing Sheets

(56)                 References Cited

U.S. PATENT DOCUMENTS

| | | | | |
|---|---|---|---|---|
| 2018/0177461 A1* | 6/2018 | Bell | ......................... | G06N 3/08 |
| 2019/0205748 A1* | 7/2019 | Fukuda | ................ | G06N 3/0464 |
| 2021/0382497 A1* | 12/2021 | Zhi | .......................... | G06T 7/73 |
| 2022/0036135 A1* | 2/2022 | Hu | ......................... | G06V 20/70 |
| 2023/0215003 A1* | 7/2023 | Tsujimoto | ........... | G06N 3/0475 |
| | | | | 382/128 |

OTHER PUBLICATIONS

Zhang et al., "Artificial Intelligence Medical Ultrasound Equipment: Application of Breast Lesions Detection," Ultrasonic Imaging, 2020, vol. 42(4-5) 191-202 (Year: 2020).*

Ronneberger et al., "U-Net: Convolutional Networks for Biomedical Image Segmentation," arXiv:1505.04597v1 [cs.CV] May 18, 2015 (Year: 2015).*

Hung et al., "Weakly- and Semi-Supervised Probabilistic Segmentation and Quantification of Ultrasound Needle-Reverberation Artifacts to Allow Better AI Understanding of Tissue Beneath Needles", arXIV:2011.11958v1, Nov. 24, 2020, 8 pages.

Hung et al., "Weakly- and Semi-Supervised Probabilistic Segmentation and Quantification of Ultrasound Needle-Reverberation Artifacts to Allow Better AI Understanding of Tissue Beneath Needles", arXiv:2011.11958v2, Jun. 3, 2011, 10 pages.

* cited by examiner

- ➤ Convolution
- ⤏ Skip connection
- ↘ Subsumed operations
- ↘ Up/down sampling
- ⤴ KL divergence
- ⬚ Concatenation
- ▨ Convolutional block
- ▨ Prior block
- ▨ Posterior block

SYSTEM, METHOD, AND COMPUTER PROGRAM PRODUCT FOR SEGMENTING AN IMAGE

CROSS REFERENCE TO RELATED APPLICATIONS

This application is the United States national phase of International Application No. PCT/US22/22094, filed Mar. 28, 2022, and claims priority to U.S. Provisional Patent Application No. 63/166,300, filed Mar. 26, 2021, the disclosures of which are hereby incorporated by reference in their entireties.

GOVERNMENT LICENSE RIGHTS

This invention was made with United States government support under W81XWH-19-C-0020 awarded by U.S. Army Medical Research and Development Command. The United States government has certain rights in the invention.

BACKGROUND

1. Field

This disclosure relates generally to segmenting images of a needle and, in non-limiting embodiments, to systems, methods, and computer program products for segmenting a needle in view of needle reverberation artifacts.

2. Technical Considerations

Ultrasound imaging is low in cost and safe. In addition, its real-time operation is useful for monitoring needle insertions and other clinical interventions. Ultrasound image quality has continually been improving. However, highly reflective parallel surfaces, such as needle walls, can create significant reverberation artifacts because the soundwave reverberates between the posterior and anterior surfaces of the object. When the amount of reflected energy is significant, it manifests itself as an additional echo from the same surface. The reverberation artifacts are relatively bright, looking like actual boundaries which sometimes would overlap with tissue present in the image. Such artifacts not only may be caused by needles and other metallic objects, but also might be the result of certain anatomical structures with large acoustic impedance. This kind of artifact can cloud clinicians' judgement and confuse medical image analysis algorithms (e.g., computer vision algorithms). Needle reverberation artifacts can be hard to identify at times and affect various pixel values to different degrees. The boundaries of such artifacts are ambiguous, leading to disagreement among human experts labeling the artifacts. For some pixels, it can be difficult to differentiate whether the pixel is an artifact, or to assign a percentage to the pixel indicating how much of the pixel's value is artifact or actual tissue measurement. The brightness of artifacts falls off as they get farther away from the reflective object, but the artifacts have uncertain boundaries and differing intensity distributions. Consequently, pixel-wise labeling is challenging and time consuming for annotators, who may have considerable differences in their annotations. As an example, different annotators may agree on the general location of the reverberation artifacts but disagree on the details. It can also be difficult for annotators to differentiate between reverberations when it gets farther away from the object casting the artifacts, leading to more differences in annotations.

SUMMARY

According to non-limiting embodiments or aspects, provided is a method comprising: segmenting each image in a sequence of images comprising a needle into a needle and at least one needle artifact based on processing each image with a first machine-learning model trained with a plurality of hard labels for a plurality of images, resulting in a plurality of hard-labeled images; transforming each hard-labeled image of the plurality of hard-labeled images into a soft-labeled image comprising pixel values corresponding to an effect of the at least one needle artifact, resulting in a plurality of soft-labeled images; and segmenting at least one image of the sequence of images based on processing the at least one image with a second machine-learning model trained at least partially with the plurality of soft-labeled images.

In non-limiting embodiments or aspects, wherein each hard label of the plurality of labels identifies a pixel or region as one of: a needle, a needle artifact, or not a needle or artifact. In non-limiting embodiments or aspects, the first machine-learning model is configured to generate a mean map for each of the needle and the at least one needle artifact, and generate a standard deviation map for each of the needle and the at least one needle artifact. In non-limiting embodiments or aspects, wherein transforming each hard-labeled image comprises transforming the mean map for the needle and the mean map for the at least one artifact into a soft-labeling mask, each soft-labeled image based on the soft-labeling mask. In non-limiting embodiments or aspects, the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster. In non-limiting embodiments or aspects, the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts.

In non-limiting embodiments or aspects, the at least one artifact comprises at least one needle reverberation artifact. In non-limiting embodiments or aspects, wherein transforming each hard-labeled image comprises: adjusting the pixel values in each image based on a calculated exponential decay. In non-limiting embodiments or aspects, the at least one needle artifact comprises a plurality of needle reverberation artifacts, and wherein adjusting the pixel values comprises lowering one or more pixel values of pixels located between needle reverberation artifacts of the plurality of needle reverberation artifacts. In non-limiting embodiments or aspects, the second machine-learning model comprises a U-Net architecture. In non-limiting embodiments or aspects, the U-Net architecture comprises a plurality of encoder blocks and a plurality of decoder blocks, the plurality of encoder blocks comprising two variational autoencoders. In non-limiting embodiments or aspects, the second machine-learning model is structured as shown in FIG. 5 and FIG. 6. In non-limiting embodiments or aspects, wherein an output of the second machine-learning model comprises a representation of how much each pixel value of a plurality of pixel values of each image is corrupted by the at least one artifact. In non-limiting embodiments or aspects, the method further comprises: training the second machine-learning model based on the plurality of soft-labeled images and a mean-squared-error-based loss function.

According to non-limiting embodiments or aspects, provided is a method of compounding images, comprising: combining pixel values for each of at least two images of different views of a subject based on multiple scaled versions of the at least two images and surrounding pixel information; and forming a single image based on the combined pixel values for a plurality of pixels in the at least two images.

In non-limiting embodiments or aspects, wherein combining pixel values is based at least partially on confidence values of at least two pixels being combined from the at least two images. In non-limiting embodiments or aspects, wherein combining pixel values is based at least partially on local contrast of at least two pixels or patches of pixels being combined from the at least two images. In non-limiting embodiments or aspects, wherein combining pixel values is based at least partially on a classification of an object in the at least two images and corresponding to the pixel values. In non-limiting embodiments or aspects, wherein combining pixel values comprises removing discrepancies based on a Laplacian image pyramid. In non-limiting embodiments or aspects, wherein combining pixel values comprises: generating an intensity and structural confidence map for each image of the at least two images; generating a Laplacian pyramid and a Gaussian pyramid of each image, the Laplacian pyramid and the Gaussian pyramid representing multiple scaled versions of the at least two images; generating a Gaussian pyramid of the intensity and structural confidence map for each image; determining a scale corresponding to a layer of the Laplacian pyramid of each image, the Gaussian pyramid of each image, and the Gaussian pyramid of the intensity and structural confidence map of each image; determining if a difference of structural confidence values of different images at the layer satisfies a threshold; selecting a pixel value for the scale of a compounded Laplacian pyramid based on if the difference satisfies the threshold; and reconstructing the compounded image based on combining scales of the compounded Laplacian pyramid. In non-limiting embodiments or aspects, the method further comprises; detecting edges of at least one boundary of at least one object in each image of the at least two images; determining a plurality of pixels representing the at least one object in each image of the at least two images; clustering at least a portion of the pixels of the plurality of pixels, resulting in a plurality of clusters in each image; and determining the at least one boundary of the at least one object based on the plurality of clusters. In non-limiting embodiments or aspects, wherein clustering the at least a portion of the pixels comprises: grouping connected pixels into the plurality of clusters; removing a subset of clusters from the plurality of clusters; and refining each cluster remaining in the plurality of clusters based on a comparison of pixel values in a clustered image to an image of the at least two images.

According to non-limiting embodiments or aspects, provided is a method of generating a confidence map for an ultrasound image, comprising: determining a confidence value for each pixel of a plurality of pixels in the ultrasound image, resulting in a confidence map; and modifying the confidence value of a subset of pixels in the confidence map based on a detected object artifact in the ultrasound image, resulting in an adjusted confidence map.

In non-limiting embodiments or aspects, the confidence map comprises a directed graph of pixels in which the confidence value of each pixel in a row of the directed graph of pixels is dependent on a confidence value of a pixel in a second row above the row, and the confidence value of each pixel in a row of the directed graph of the adjusted confidence map is dependent on additional proximate pixels in the second row above the row. In non-limiting embodiments or aspects, the method further comprises: segmenting the ultrasound image to identify an object and the object artifact. In non-limiting embodiments or aspects, the object comprises a needle and the object artifact comprises a needle reverberation artifact. In non-limiting embodiments or aspects, the method further comprises: obtaining a reference intensity confidence map for a reference image captured with an ultrasound system used to capture the ultrasound image, wherein modifying the confidence value of the subset of pixels is based on comparing pixel values from the reference intensity confidence map to the confidence map.

According to non-limiting embodiments or aspects, provided is a system comprising at least one computing device programmed or configured to: segment each image in a sequence of images comprising a needle into a needle and at least one needle artifact based on processing each image with a first machine-learning model trained with a plurality of hard labels for a plurality of images, resulting in a plurality of hard-labeled images; transform each hard-labeled image of the plurality of hard-labeled images into a soft-labeled image comprising pixel values corresponding to an effect of the at least one needle artifact, resulting in a plurality of soft-labeled images; and segment at least one image of the sequence of images based on processing the at least one image with a second machine-learning model trained at least partially with the plurality of soft-labeled images.

In non-limiting embodiments or aspects, wherein each hard label of the plurality of labels identifies a pixel or region as one of: a needle, a needle artifact, or not a needle or artifact. In non-limiting embodiments or aspects, the first machine-learning model is configured to generate a mean map for each of the needle and the at least one needle artifact, and generate a standard deviation map for each of the needle and the at least one needle artifact. In non-limiting embodiments or aspects, wherein transforming each hard-labeled image comprises transforming the mean map for the needle and the mean map for the at least one artifact into a soft-labeling mask, each soft-labeled image based on the soft-labeling mask. In non-limiting embodiments or aspects, the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster. In non-limiting embodiments or aspects, the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts. In non-limiting embodiments or aspects, the at least one artifact comprises at least one needle reverberation artifact. In non-limiting embodiments or aspects, wherein transforming each hard-labeled image comprises: adjusting the pixel values in each image based on a calculated exponential decay. In non-limiting embodiments or aspects, the at least one needle artifact comprises a plurality of needle reverberation artifacts, and wherein adjusting the pixel values comprises lowering one or more pixel values of pixels located between needle reverberation artifacts of the plurality of needle reverberation artifacts. In non-limiting embodiments or aspects, the second machine-learning model comprises a U-Net architecture. In non-limiting embodiments or aspects, the U-Net architecture comprises a plurality of encoder blocks and a plurality of decoder blocks, the plurality of encoder blocks comprising two variational autoencoders. In non-limiting embodiments or aspects, the second machine-learning model is structured as shown in FIG. 5 and FIG. 6. In non-limiting embodiments or aspects, wherein an output of the second machine-learning model comprises a representation of how much each pixel value of a plurality of pixel values of each image is corrupted by the at least one artifact. In non-limiting embodiments or aspects, the computing device further configured to: train the second machine-learning model based on the plurality of soft-labeled images and a mean-squared-error-based loss function.

According to non-limiting embodiments or aspects, provided is a system of compounding images, comprising: combine pixel values for each of at least two images of different views of a subject based on multiple scaled versions of the at least two images and surrounding pixel information; and form a single image based on the combined pixel values for a plurality of pixels in the at least two images.

In non-limiting embodiments or aspects, wherein combining pixel values is based at least partially on confidence values of at least two pixels being combined from the at least two images. In non-limiting embodiments or aspects, wherein combining pixel values is based at least partially on local contrast of at least two pixels or patches of pixels being combined from the at least two images. In non-limiting embodiments or aspects, wherein combining pixel values is based at least partially on a classification of an object in the at least two images and corresponding to the pixel values. In non-limiting embodiments or aspects, wherein combining pixel values comprises removing discrepancies based on a Laplacian image pyramid. In non-limiting embodiments or aspects, wherein combining pixel values comprises: generate an intensity and structural confidence map for each image of the at least two images; generate a Laplacian pyramid and a Gaussian pyramid of each image, the Laplacian pyramid and the Gaussian pyramid representing multiple scaled versions of the at least two images; generate a Gaussian pyramid of the intensity and structural confidence map for each image; determine a scale corresponding to a layer of the Laplacian pyramid of each image, the Gaussian pyramid of each image, and the Gaussian pyramid of the intensity and structural confidence map of each image; determine if a difference of structural confidence values of different images at the layer satisfies a threshold; select a pixel value for the scale of a compounded Laplacian pyramid based on if the difference satisfies the threshold; and reconstruct the compounded image based on combining scales of the compounded Laplacian pyramid. In non-limiting embodiments or aspects, the computing device further configured to: detect edges of at least one boundary of at least one object in each image of the at least two images; determine a plurality of pixels representing the at least one object in each image of the at least two images; cluster at least a portion of the pixels of the plurality of pixels, resulting in a plurality of clusters in each image; and determine the at least one boundary of the at least one object based on the plurality of clusters. In non-limiting embodiments or aspects, wherein clustering the at least a portion of the pixels comprises: grouping connected pixels into the plurality of clusters; removing a subset of clusters from the plurality of clusters; and refining each cluster remaining in the plurality of clusters based on a comparison of pixel values in a clustered image to an image of the at least two images.

According to non-limiting embodiments or aspects, provided is a system of generating a confidence map for an ultrasound image, comprising: determine a confidence value for each pixel of a plurality of pixels in the ultrasound image, resulting in a confidence map; and modify the confidence value of a subset of pixels in the confidence map based on a detected object artifact in the ultrasound image, resulting in an adjusted confidence map.

In non-limiting embodiments or aspects, the confidence map comprises a directed graph of pixels in which the confidence value of each pixel in a row of the directed graph of pixels is dependent on a confidence value of a pixel in a second row above the row, and the confidence value of each pixel in a row of the directed graph of the adjusted confidence map is dependent on additional proximate pixels in the second row above the row. In non-limiting embodiments or aspects, the computing device further configured to: segment the ultrasound image to identify an object and the object artifact. In non-limiting embodiments or aspects, the object comprises a needle and the object artifact comprises a needle reverberation artifact. In non-limiting embodiments or aspects, the computing device further configured to: obtain a reference intensity confidence map for a reference image captured with an ultrasound system used to capture the ultrasound image, wherein modifying the confidence value of the subset of pixels is based on comparing pixel values from the reference intensity confidence map to the confidence map.

According to non-limiting embodiments or aspects, provided is a computer program product comprising at least one non-transitory computer-readable medium including instructions that, when executed by at least one computing device, cause the at least one computing device to: segment each image in a sequence of images comprising a needle into a needle and at least one needle artifact based on processing each image with a first machine-learning model trained with a plurality of hard labels for a plurality of images, resulting in a plurality of hard-labeled images; transform each hard-labeled image of the plurality of hard-labeled images into a soft-labeled image comprising pixel values corresponding to an effect of the at least one needle artifact, resulting in a plurality of soft-labeled images; and segment at least one image of the sequence of images based on processing the at least one image with a second machine-learning model trained at least partially with the plurality of soft-labeled images.

In non-limiting embodiments or aspects, wherein each hard label of the plurality of labels identifies a pixel or region as one of: a needle, a needle artifact, or not a needle or artifact. In non-limiting embodiments or aspects, the first machine-learning model is configured to generate a mean map for each of the needle and the at least one needle artifact, and generate a standard deviation map for each of the needle and the at least one needle artifact. In non-limiting embodiments or aspects, wherein transforming each hard-labeled image comprises transforming the mean map for the needle and the mean map for the at least one artifact into a soft-labeling mask, each soft-labeled image based on the soft-labeling mask. In non-limiting embodiments or aspects, the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster. In non-limiting embodiments or aspects, the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts. In non-limiting embodiments or aspects, the at least one artifact comprises at least one needle reverberation artifact. In non-limiting embodiments or aspects, wherein transforming each hard-labeled image comprises: adjusting the pixel values in each image based on a calculated exponential decay. In non-limiting embodiments or aspects, and wherein adjusting the pixel values comprises lowering one or more pixel values of pixels located between needle reverberation artifacts of the plurality of needle reverberation artifacts. In non-limiting embodiments or aspects, the second machine-learning model comprises a U-Net architecture. In non-limiting embodiments or aspects, the U-Net architecture comprises a plurality of encoder blocks and a plurality of decoder blocks, the plurality of encoder blocks comprising two variational autoencoders. In non-limiting embodiments or aspects, the second machine-learning model is structured as shown in FIG. 5 and FIG. 6. In non-limiting embodiments or aspects, wherein an output of the second machine-learning model comprises a representation of how much each pixel value of a plurality of pixel values of each image is corrupted by the at least one artifact. In non-limiting embodiments or aspects, the computing device further configured to: train the second machine-learning model based on the plurality of soft-labeled images and a mean-squared-error-based loss function.

According to non-limiting embodiments or aspects, provided is a computer program product of compounding images, comprising at least one non-transitory computer-readable medium including instructions that, when executed by at least one computing device, cause the at least one computing device to: combine pixel values for each of at least two images of different views of a subject based on multiple scaled versions of the at least two images and surrounding pixel information; and form a single image based on the combined pixel values for a plurality of pixels in the at least two images.

In non-limiting embodiments or aspects, wherein combining pixel values is based at least partially on confidence values of at least two pixels being combined from the at least two images. In non-limiting embodiments or aspects, wherein combining pixel values is based at least partially on local contrast of at least two pixels or patches of pixels being combined from the at least two images. In non-limiting embodiments or aspects, wherein combining pixel values is based at least partially on a classification of an object in the at least two images and corresponding to the pixel values. In non-limiting embodiments or aspects, wherein combining pixel values comprises removing discrepancies based on a Laplacian image pyramid. In non-limiting embodiments or aspects, wherein combining pixel values comprises: generate an intensity and structural confidence map for each image of the at least two images; generate a Laplacian pyramid and a Gaussian pyramid of each image, the Laplacian pyramid and the Gaussian pyramid representing multiple scaled versions of the at least two images; generate a Gaussian pyramid of the intensity and structural confidence map for each image; determine a scale corresponding to a layer of the Laplacian pyramid of each image, the Gaussian pyramid of each image, and the Gaussian pyramid of the intensity and structural confidence map of each image; determine if a difference of structural confidence values of different images at the layer satisfies a threshold; select a pixel value for the scale of a compounded Laplacian pyramid based on if the difference satisfies the threshold; and reconstruct the compounded image based on combining scales of the compounded Laplacian pyramid. In non-limiting embodiments or aspects, the computing device further caused to: detect edges of at least one boundary of at least one object in each image of the at least two images; determine a plurality of pixels representing the at least one object in each image of the at least two images; cluster at least a portion of the pixels of the plurality of pixels, resulting in a plurality of clusters in each image; and determine the at least one boundary of the at least one object based on the plurality of clusters. In non-limiting embodiments or aspects, wherein clustering the at least a portion of the pixels comprises: grouping connected pixels into the plurality of clusters; removing a subset of clusters from the plurality of clusters; and refining each cluster remaining in the plurality of clusters based on a comparison of pixel values in a clustered image to an image of the at least two images.

According to non-limiting embodiments or aspects, provided is a computer program product of generating a confidence map for an ultrasound image, comprising at least one non-transitory computer-readable medium including instructions that, when executed by at least one computing device, cause the at least one computing device to: determine a confidence value for each pixel of a plurality of pixels in the ultrasound image, resulting in a confidence map; and modify the confidence value of a subset of pixels in the confidence map based on a detected object artifact in the ultrasound image, resulting in an adjusted confidence map.

In non-limiting embodiments or aspects, the confidence map comprises a directed graph of pixels in which the confidence value of each pixel in a row of the directed graph of pixels is dependent on a confidence value of a pixel in a second row above the row, and the confidence value of each pixel in a row of the directed graph of the adjusted confidence map is dependent on additional proximate pixels in the second row above the row. In non-limiting embodiments or aspects, the computing device further caused to: segment the ultrasound image to identify an object and the object artifact. In non-limiting embodiments or aspects, the object comprises a needle and the object artifact comprises a needle reverberation artifact. In non-limiting embodiments or aspects, the computing device further configured to: obtain a reference intensity confidence map for a reference image captured with an ultrasound computer program product used to capture the ultrasound image, wherein modifying the confidence value of the subset of pixels is based on comparing pixel values from the reference intensity confidence map to the confidence map.

Further non-limiting embodiments are set forth in the following numbered clauses:

Clause 1: A method comprising: segmenting each image in a sequence of images comprising a needle into a needle and at least one needle artifact based on processing each image with a first machine-learning model trained with a plurality of hard labels for a plurality of images, resulting in a plurality of hard-labeled images; transforming each hard-labeled image of the plurality of hard-labeled images into a soft-labeled image comprising pixel values corresponding to an effect of the at least one needle artifact, resulting in a plurality of soft-labeled images; and segmenting at least one image of the sequence of images based on processing the at least one image with a second machine-learning model trained at least partially with the plurality of soft-labeled images.

Clause 2: The method of clause 1, wherein each hard label of the plurality of labels identifies a pixel or region as one of: a needle, a needle artifact, or not a needle or artifact.

Clause 3: The method of clauses 1 or 2, wherein the first machine-learning model is configured to generate a mean map for each of the needle and the at least one needle artifact, and generate a standard deviation map for each of the needle and the at least one needle artifact.

Clause 4: The method of any of clauses 1-3, wherein transforming each hard-labeled image comprises transforming the mean map for the needle and the mean map for the at least one artifact into a soft-labeling mask, each soft-labeled image based on the soft-labeling mask.

Clause 5: The method of any of clauses 1-4, wherein the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster.

Clause 6: The method of any of clauses 1-5, wherein the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts.

Clause 7: The method of any of clauses 1-6, wherein the at least one artifact comprises at least one needle reverberation artifact.

Clause 8: The method of any of clauses 1-7, wherein transforming each hard-labeled image comprises: adjusting the pixel values in each image based on a calculated exponential decay.

Clause 9: The method of any of clauses 1-8, wherein the at least one needle artifact comprises a plurality of needle reverberation artifacts, and wherein adjusting the pixel values comprises lowering one or more pixel values of pixels located between needle reverberation artifacts of the plurality of needle reverberation artifacts.

Clause 10: The method of any of clauses 1-9, wherein the second machine-learning model comprises a U-Net architecture.

Clause 11: The method of any of clauses 1-10, wherein the U-Net architecture comprises a plurality of encoder blocks and a plurality of decoder blocks, the plurality of encoder blocks comprising two variational autoencoders.

Clause 12: The method of any of clauses 1-11, wherein the second machine-learning model is structured as shown in FIG. 5 and FIG. 6.

Clause 13: The method of any of clauses 1-12, wherein an output of the second machine-learning model comprises a representation of how much each pixel value of a plurality of pixel values of each image is corrupted by the at least one artifact.

Clause 14: The method of any of clauses 1-13, further comprising: training the second machine-learning model based on the plurality of soft-labeled images and a mean-squared-error-based loss function.

Clause 15: A method of compounding images, comprising: combining pixel values for each of at least two images of different views of a subject based on multiple scaled versions of the at least two images and surrounding pixel information; and forming a single image based on the combined pixel values for a plurality of pixels in the at least two images.

Clause 16. The method of clause 15, wherein combining pixel values is based at least partially on confidence values of at least two pixels being combined from the at least two images.

Clause 17: The method of clauses 15 or 16, wherein combining pixel values is based at least partially on local contrast of at least two pixels or patches of pixels being combined from the at least two images.

Clause 18: The method of any of clauses 15-17, wherein combining pixel values is based at least partially on a classification of an object in the at least two images and corresponding to the pixel values.

Clause 19: The method of any of clauses 15-18, wherein combining pixel values comprises removing discrepancies based on a Laplacian image pyramid.

Clause 20: The method of any of clauses 15-19, wherein combining pixel values comprises: generating an intensity and structural confidence map for each image of the at least two images; generating a Laplacian pyramid and a Gaussian pyramid of each image, the Laplacian pyramid and the Gaussian pyramid representing multiple scaled versions of the at least two images; generating a Gaussian pyramid of the intensity and structural confidence map for each image; determining a scale corresponding to a layer of the Laplacian pyramid of each image, the Gaussian pyramid of each image, and the Gaussian pyramid of the intensity and structural confidence map of each image; determining if a difference of structural confidence values of different images at the layer satisfies a threshold; selecting a pixel value for the scale of a compounded Laplacian pyramid based on if the difference satisfies the threshold; and reconstructing the compounded image based on combining scales of the compounded Laplacian pyramid.

Clause 21: The method of any of clauses 15-20, further comprising; detecting edges of at least one boundary of at least one object in each image of the at least two images; determining a plurality of pixels representing the at least one object in each image of the at least two images; clustering at least a portion of the pixels of the plurality of pixels, resulting in a plurality of clusters in each image; and determining the at least one boundary of the at least one object based on the plurality of clusters.

Clause 22: The method of any of clauses 15-21, wherein clustering the at least a portion of the pixels comprises:

grouping connected pixels into the plurality of clusters; removing a subset of clusters from the plurality of clusters; and refining each cluster remaining in the plurality of clusters based on a comparison of pixel values in a clustered image to an image of the at least two images.

Clause 23: A method of generating a confidence map for an ultrasound image, comprising: determining a confidence value for each pixel of a plurality of pixels in the ultrasound image, resulting in a confidence map; and modifying the confidence value of a subset of pixels in the confidence map based on a detected object artifact in the ultrasound image, resulting in an adjusted confidence map.

Clause 24: The method of clause 23, wherein the confidence map comprises a directed graph of pixels in which the confidence value of each pixel in a row of the directed graph of pixels is dependent on a confidence value of a pixel in a second row above the row, and wherein the confidence value of each pixel in a row of the directed graph of the adjusted confidence map is dependent on additional proximate pixels in the second row above the row.

Clause 25: The method of clauses 23 or 24, further comprising: segmenting the ultrasound image to identify an object and the object artifact.

Clause 26: The method of any of clauses 23-25, wherein the object comprises a needle and the object artifact comprises a needle reverberation artifact.

Clause 27: The method of any of clauses 23-26, further comprising: obtaining a reference intensity confidence map for a reference image captured with an ultrasound system used to capture the ultrasound image, wherein modifying the confidence value of the subset of pixels is based on comparing pixel values from the reference intensity confidence map to the confidence map.

Clause 28: A system comprising at least one computing device programmed or configured to: segment each image in a sequence of images comprising a needle into a needle and at least one needle artifact based on processing each image with a first machine-learning model trained with a plurality of hard labels for a plurality of images, resulting in a plurality of hard-labeled images; transform each hard-labeled image of the plurality of hard-labeled images into a soft-labeled image comprising pixel values corresponding to an effect of the at least one needle artifact, resulting in a plurality of soft-labeled images; and segment at least one image of the sequence of images based on processing the at least one image with a second machine-learning model trained at least partially with the plurality of soft-labeled images.

Clause 29: The system of clause 28, wherein each hard label of the plurality of labels identifies a pixel or region as one of: a needle, a needle artifact, or not a needle or artifact.

Clause 30: The system of clauses 28 or 29, wherein the first machine-learning model is configured to generate a mean map for each of the needle and the at least one needle artifact, and generate a standard deviation map for each of the needle and the at least one needle artifact.

Clause 31: The system of any of clauses 28-30, wherein transforming each hard-labeled image comprises transforming the mean map for the needle and the mean map for the at least one artifact into a soft-labeling mask, each soft-labeled image based on the soft-labeling mask.

Clause 32: The system of any of clauses 28-31, wherein the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster.

Clause 33: The system of any of clauses 28-32, wherein the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts.

Clause 34: The system of any of clauses 28-33, wherein the at least one artifact comprises at least one needle reverberation artifact.

Clause 35: The system of any of clauses 28-34, wherein transforming each hard-labeled image comprises: adjusting the pixel values in each image based on a calculated exponential decay.

Clause 36: The system of any of clauses 28-35, wherein the at least one needle artifact comprises a plurality of needle reverberation artifacts, and wherein adjusting the pixel values comprises lowering one or more pixel values of pixels located between needle reverberation artifacts of the plurality of needle reverberation artifacts.

Clause 37: The system of any of clauses 28-36, wherein the second machine-learning model comprises a U-Net architecture.

Clause 38: The system of any of clauses 28-37, wherein the U-Net architecture comprises a plurality of encoder blocks and a plurality of decoder blocks, the plurality of encoder blocks comprising two variational autoencoders.

Clause 39: The system of any of clauses 28-38, wherein the second machine-learning model is structured as shown in FIG. 5 and FIG. 6.

Clause 40: The system of any of clauses 28-39, wherein an output of the second machine-learning model comprises a representation of how much each pixel value of a plurality of pixel values of each image is corrupted by the at least one artifact.

Clause 41: The system of any of clauses 28-40, the computing device further configured to: train the second machine-learning model based on the plurality of soft-labeled images and a mean-squared-error-based loss function.

Clause 42: A system of compounding images, comprising: combine pixel values for each of at least two images of different views of a subject based on multiple scaled versions of the at least two images and surrounding pixel information; and form a single image based on the combined pixel values for a plurality of pixels in the at least two images.

Clause 43: The system of clause 42, wherein combining pixel values is based at least partially on confidence values of at least two pixels being combined from the at least two images.

Clause 44: The system of clauses 42 or 43, wherein combining pixel values is based at least partially on local contrast of at least two pixels or patches of pixels being combined from the at least two images.

Clause 45: The system of any of clauses 42-44, wherein combining pixel values is based at least partially on a classification of an object in the at least two images and corresponding to the pixel values.

Clause 46: The system of any of clauses 42-45, wherein combining pixel values comprises removing discrepancies based on a Laplacian image pyramid.

Clause 47: The system of any of clauses 42-46, wherein combining pixel values comprises: generate an intensity and structural confidence map for each image of the at least two images; generate a Laplacian pyramid and a Gaussian pyramid of each image, the Laplacian pyramid and the Gaussian pyramid representing multiple scaled versions of the at least two images; generate a Gaussian pyramid of the intensity and structural confidence map for each image; determine a scale corresponding to a layer of the Laplacian pyramid of each image, the Gaussian pyramid of each image, and the Gaussian pyramid of the intensity and structural confidence map of each image; determine if a difference of structural confidence values of different images at the layer satisfies a threshold; select a pixel value for the scale of a compounded Laplacian pyramid based on if the difference satisfies the threshold; and reconstruct the compounded image based on combining scales of the compounded Laplacian pyramid.

Clause 48: The system of any of clauses 42-47, the computing device further configured to: detect edges of at least one boundary of at least one object in each image of the at least two images; determine a plurality of pixels representing the at least one object in each image of the at least two images; cluster at least a portion of the pixels in the plurality of pixels, resulting in a plurality of clusters in each image; and determine the at least one boundary of the at least one object based on the plurality of clusters.

Clause 49: The system of any of clauses 42-48, wherein clustering the at least a portion of the pixels comprises: grouping connected pixels into the plurality of clusters; removing a subset of clusters from the plurality of clusters; and refining each cluster remaining in the plurality of clusters based on a comparison of pixel values in a clustered image to an image of the at least two images.

Clause 50: A system of generating a confidence map for an ultrasound image, comprising: determine a confidence value for each pixel of a plurality of pixels in the ultrasound image, resulting in a confidence map; and modify the confidence value of a subset of pixels in the confidence map based on a detected object artifact in the ultrasound image, resulting in an adjusted confidence map.

Clause 51: The system of clause 50, wherein the confidence map comprises a directed graph of pixels in which the confidence value of each pixel in a row of the directed graph of pixels is dependent on a confidence value of a pixel in a second row above the row, and wherein the confidence value of each pixel in a row of the directed graph of the adjusted confidence map is dependent on additional proximate pixels in the second row above the row.

Clause 52: The system of clauses 50 or 51, the computing device further configured to: segment the ultrasound image to identify an object and the object artifact.

Clause 53: The system of any of clauses 50-52, wherein the object comprises a needle and the object artifact comprises a needle reverberation artifact.

Clause 54: The system of any of clauses 50-53, the computing device further configured to: obtain a reference intensity confidence map for a reference image captured with an ultrasound system used to capture the ultrasound image, wherein modifying the confidence value of the subset of pixels is based on comparing pixel values from the reference intensity confidence map to the confidence map.

Clause 55: A computer program product comprising at least one non-transitory computer-readable medium including instructions that, when executed by at least one computing device, cause the at least one computing device to: segment each image in a sequence of images comprising a needle into a needle and at least one needle artifact based on processing each image with a first machine-learning model trained with a plurality of hard labels for a plurality of images, resulting in a plurality of hard-labeled images; transform each hard-labeled image of the plurality of hard-labeled images into a soft-labeled image comprising pixel values corresponding to an effect of the at least one needle artifact, resulting in a plurality of soft-labeled images; and segment at least one image of the sequence of images based on processing the at least one image with a second machine-learning model trained at least partially with the plurality of soft-labeled images.

Clause 56: The computer program product of clause 55, wherein each hard label of the plurality of labels identifies a pixel or region as one of: a needle, a needle artifact, or not a needle or artifact.

Clause 57: The computer program product of clauses 55 or 56, wherein the first machine-learning model is configured to generate a mean map for each of the needle and the at least one needle artifact, and generate a standard deviation map for each of the needle and the at least one needle artifact.

Clause 58: The computer program product of any of clauses 55-57, wherein transforming each hard-labeled image comprises transforming the mean map for the needle and the mean map for the at least one artifact into a soft-labeling mask, each soft-labeled image based on the soft-labeling mask.

Clause 59: The computer program product of any of clauses 55-58, wherein the at least one needle artifact comprises a plurality of needle artifacts, and wherein transforming each hard-labeled image comprises: clustering the plurality of needle artifacts based on a distance between needle artifacts, resulting in at least one cluster; determining if the needle is above each cluster of the at least one cluster; and in response to determining that the needle is above a cluster, maintain artifacts in the cluster.

Clause 60: The computer program product of any of clauses 55-59, wherein the at least one needle artifact comprises a plurality of needle artifacts, and wherein transforming each hard-labeled image comprises: clustering the plurality of needle artifacts based on a distance between artifacts, resulting in at least one cluster; determining if the needle is above each cluster of the at least one cluster; and in response to determining that the needle is not above the cluster, remove the needle artifacts in the cluster from the plurality of artifacts.

Clause 61: The computer program product of any of clauses 55-60, wherein the at least one artifact comprises at least one needle reverberation artifact.

Clause 62: The computer program product of any of clauses 55-61, wherein transforming each hard-labeled image comprises: adjusting the pixel values in each image based on a calculated exponential decay.

Clause 63: The computer program product of any of clauses 55-62, wherein adjusting the pixel values comprises lowering one or more pixel values of pixels located between needle reverberation artifacts of the plurality of needle reverberation artifacts.

Clause 64: The computer program product of any of clauses 55-63, wherein the second machine-learning model comprises a U-Net architecture.

Clause 65: The computer program product of any of clauses 55-64, wherein the U-Net architecture comprises a plurality of encoder blocks and a plurality of decoder blocks, the plurality of encoder blocks comprising two variational autoencoders.

Clause 66: The computer program product of any of clauses 55-65, wherein the second machine-learning model is structured as shown in FIG. 5 and FIG. 6.

Clause 67: The computer program product of any of clauses 55-66, wherein an output of the second machine-learning model comprises a representation of how much each pixel value of a plurality of pixel values of each image is corrupted by the at least one artifact.

Clause 68: The computer program product of any of clauses 55-67, the computing device further configured to: train the second machine-learning model based on the plurality of soft-labeled images and a mean-squared-error-based loss function.

Clause 69: A computer program product of compounding images, comprising at least one non-transitory computer-readable medium including instructions that, when executed by at least one computing device, cause the at least one computing device to: combine pixel values for each of at least two images of different views of a subject based on multiple scaled versions of the at least two images and surrounding pixel information; and form a single image based on the combined pixel values for a plurality of pixels in the at least two images.

Clause 70: The computer program product of clause 69, wherein combining pixel values is based at least partially on confidence values of at least two pixels being combined from the at least two images.

Clause 71: The computer program product of clauses 69 or 70, wherein combining pixel values is based at least partially on local contrast of at least two pixels or patches of pixels being combined from the at least two images.

Clause 72: The computer program product of any of clauses 69-71, wherein combining pixel values is based at least partially on a classification of an object in the at least two images and corresponding to the pixel values.

Clause 73: The computer program product of any of clauses 69-72, wherein combining pixel values comprises removing discrepancies based on a Laplacian image pyramid.

Clause 74: The computer program product of any of clauses 69-73, wherein combining pixel values comprises: generate an intensity and structural confidence map for each image of the at least two images; generate a Laplacian pyramid and a Gaussian pyramid of each image, the Laplacian pyramid and the Gaussian pyramid representing multiple scaled versions of the at least two images; generate a Gaussian pyramid of the intensity and structural confidence map for each image; determine a scale corresponding to a layer of the Laplacian pyramid of each image, the Gaussian pyramid of each image, and the Gaussian pyramid of the intensity and structural confidence map of each image; determine if a difference of structural confidence values of different images at the layer satisfies a threshold; select a pixel value for the scale of a compounded Laplacian pyramid based on if the difference satisfies the threshold; and reconstruct the compounded image based on combining scales of the compounded Laplacian pyramid.

Clause 75: The computer program product of any of clauses 69-74, the computing device further caused to: detect edges of at least one boundary of at least one object in each image of the at least two images; determine a plurality of pixels representing the at least one object in each image of the at least two images; cluster at least a portion of the pixels of the plurality of pixels, resulting in a plurality of clusters in each image; and determine the at least one boundary of the at least one object based on the plurality of clusters.

Clause 76: The computer program product of any of clauses 69-75, wherein clustering the at least a portion of the pixels comprises: grouping connected pixels into the plurality of clusters; removing a subset of clusters from the plurality of clusters; and refining each cluster remaining in the plurality of clusters based on a comparison of pixel values in a clustered image to an image of the at least two images.

Clause 77: A computer program product of generating a confidence map for an ultrasound image, comprising at least one non-transitory computer-readable medium including instructions that, when executed by at least one computing device, cause the at least one computing device to: determine a confidence value for each pixel of a plurality of pixels in the ultrasound image, resulting in a confidence map; and modify the confidence value of a subset of pixels in the confidence map based on a detected object artifact in the ultrasound image, resulting in an adjusted confidence map.

Clause 78: The computer program product of clause 77, wherein the confidence map comprises a directed graph of pixels in which the confidence value of each pixel in a row of the directed graph of pixels is dependent on a confidence value of a pixel in a second row above the row, and wherein the confidence value of each pixel in a row of the directed graph of the adjusted confidence map is dependent on additional proximate pixels in the second row above the row.

Clause 79: The computer program product of clauses 77 or 78, the computing device further caused to: segment the ultrasound image to identify an object and the object artifact.

Clause 80: The computer program product of any of clauses 77-79, wherein the object comprises a needle and the object artifact comprises a needle reverberation artifact.

Clause 81: The computer program product of any of clauses 77-80, the computing device further configured to: obtain a reference intensity confidence map for a reference image captured with an ultrasound computer program product used to capture the ultrasound image, wherein modifying the confidence value of the subset of pixels is based on comparing pixel values from the reference intensity confidence map to the confidence map.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying drawings, in which.

DETAILED DESCRIPTION

It is to be understood that the embodiments may assume various alternative variations and step sequences, except where expressly specified to the contrary. It is also to be understood that the specific devices and processes described in the following specification are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include an artificial intelligence (AI) accelerator, including an application-specific integrated circuit (ASIC) neural engine such as Apple's M1® "Neural Engine" or Google's TENSOR-FLOW® processing unit. In non-limiting embodiments, a computing device may be comprised of a plurality of individual circuits.

As used herein, the term "subject" may refer to a person (e.g., a human body), an animal, a medical patient, and/or the like. A subject may have a skin or skin-like surface.

Figure 1:
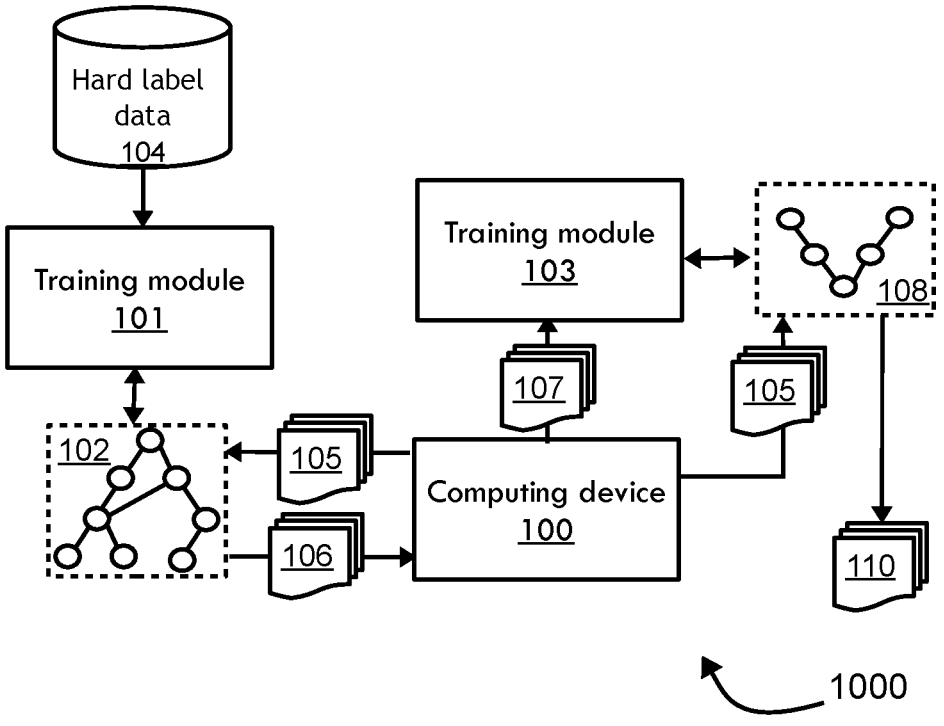
FIG. 1 illustrates a system for segmenting images of a needle according to non-limiting embodiments.

FIG. 1 shows a system 1000 for segmenting images of a needle according to non-limiting embodiments. The images may be ultrasound images, although it will be appreciated that other types of images may be used and that ultrasound is used herein as an example. A sequence of images 105 represents motion of a needle being inserted into a tissue of a subject, as an example. A computing device 100 may process the sequence of images with a first machine-learning model 102, such as a probabilistic image segmentation model. The model 102 may be executed by the computing device 100 and/or another device. The model 102 may be trained with hard-labeled images (e.g., stored in hard label database 104) by training module 101, which may be part of computing device 100 or another computing device. The trained model 102 processes each image of the sequence of images 105 and outputs a plurality of hard-labeled images 106. The hard-labeled images may include labels (e.g., classifications) for each pixel to represent a needle, a needle artifact (e.g., reverberation effect), or background (e.g., neither a needle nor artifact). The hard-labeled images used for training may be manually labeled images in non-limiting embodiments.

With continued reference to FIG. 1, the computing device 100 transforms the hard-labeled images 106 into a plurality of soft-labeled images 107. The soft-labeled images 107 are used by a training module 103, which may be part of the computing device 100 or another computing device, to train a second machine-learning model 108. The second machine-learning model 108 may be a convolutional neural network in a U-Net architecture, as an example. The computing device 100 may then process the sequence of images 105 with the second machine-learning model 108. The model 108 may be executed by the computing device 100 and/or another device. The second machine-learning model outputs segmented images 110 in which the needle is distinguished from both the background of the image and any artifacts, including needle reverberation artifacts.

Figure 3:
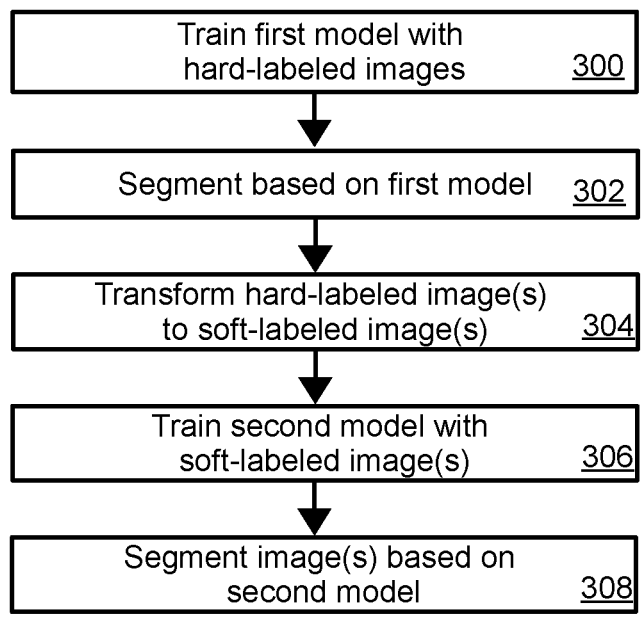
FIG. 3 illustrates a flow diagram for a method of segmenting images of a needle according to non-limiting embodiments.

Referring now to FIG. 3, a flow diagram is shown for a method of segmenting images of a needle according to non-limiting embodiments. The steps shown in FIG. 3 are for example purposes only. It will be appreciated that additional, fewer, different, and/or a different order of steps may be used in non-limiting embodiments. At a first step 300, a first machine-learning model is trained, such as a probabilistic image segmentation model. The hard-labeled images may be labeled by human labelers. The model may be trained with hard-labeled images with a cross entropy loss function. Once trained, the labeled training data may not be needed to process an image for segmentation.

At step 302, an image in a sequence of images is segmented based on the first machine-learning model. The objects (e.g., artifacts) might differ by shape, intensity distribution, and unclear boundaries so human labels could be different across annotators. Even when the same annotator labels the same image multiple times, the results can still differ. In non-limiting embodiments, the segmentation algorithm applied at step 302 generates nearly identical results for the same image despite using data labeled by different annotators. In non-limiting embodiments, the model may designed with more local blocks than global blocks to better model the ambiguity of edges. The first machine-learning model may sample from a learned distribution to generate a mean map and a standard deviation map for the needle segmentation, and a mean map and a standard deviation map for the artifact segmentation. The mean maps may be referred to as $\hat{\mu}_{artifact,hard}$ and $\hat{\mu}_{needle,hard}$, and the standard deviation maps may be referred to as $\hat{\sigma}_{artifact,hard}$ and $\hat{\sigma}_{needle,hard}$.

At step 304 of FIG. 3, the hard-labeled images output by the first machine-learning model may be transformed into soft-labeled images. Even though the output of the first model inherently models the ambiguity in the input images and the human labels, it does not account for the fact that weaker reverberation artifacts do not affect the quality of the image as much as the strong ones do. Therefore, the segmentation mask (e.g., based on the maps output of the first machine-learning model) are transformed into a soft-labeling mask, which models how much the needle artifacts affect the pixel value. The transformation function executed at step 304 may reduce false positives, introduce an exponential decay depending on how far the artifact is relative to the needle causing the artifact, and lower the values for artifact-segmentation soft labels for pixels in between adjacent reverberations.

Figure 4:
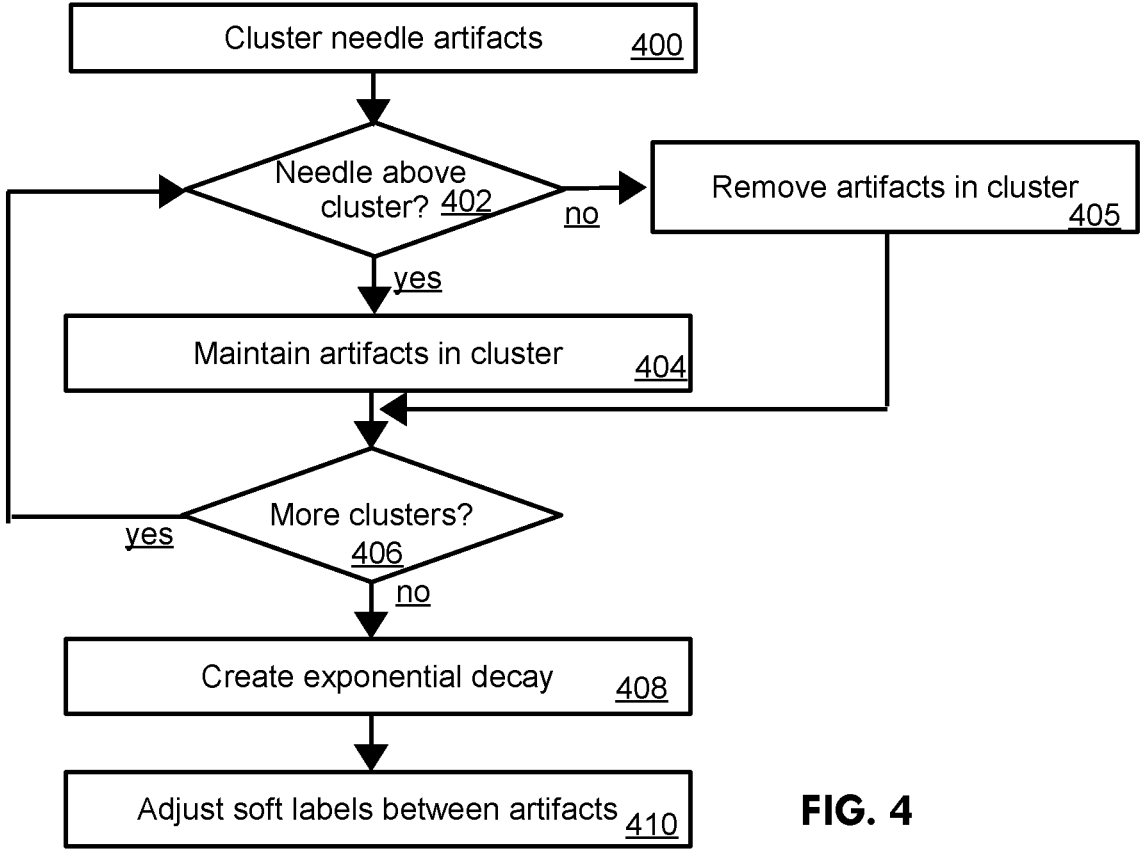
FIG. 4 illustrates a flow diagram for a method of segmenting images of a needle according to non-limiting embodiments.

Referring now to FIG. 4, a flow diagram is shown for transforming hard-labeled images into soft-labeled images according to non-limiting embodiments. FIG. 4 may, in some examples, represent step 304 of FIG. 3. The steps shown in FIG. 4 are for example purposes only. It will be appreciated that additional, fewer, different, and/or a different order of steps may be used in non-limiting embodiments. Taking in the predicted masks $\hat{\mu}_{artifact,hard}$ and $\hat{\mu}_{needle,hard}$, the process begins at step 400 by clustering the artifacts based on distance into one or more clusters. At step 402, it is determined if the segmented needle is above a cluster (e.g., above and within a distance range). If the needle is above a cluster, it is determined that the needle is the cause for the artifacts and at step 404 the artifacts in that cluster are maintained as needle artifacts. If the needle is not above a cluster, at step 405 the artifacts in that cluster are removed from the segmented image (e.g., the labels for those artifacts are changed). In examples with multiple needles, rather than being removed at step 405, the cluster may be identified for potential removal after all needles have been processed.

In non-limiting embodiments, the following algorithm may be used to perform steps 402, 404, 405, 406:

---

Algorithm 1:

---

Data: $\hat{\mu}_{needle,hard}$, $\hat{\mu}_{artifact,hard}$
Result: $y_1$: artifact mask with false positives removed
size = input image size
B = zeros(size), $y_1$ = zeros(size); k = 1;
for [row i, column j] where $\hat{\mu}_{artifact,hard}[i, j] > 0$ do
| if B[i, j] = = 0 then
| | create stack s;
| | s.push([i, j]); B[i, j] = k;
| | while s is not empty do
| | | [x, y] = s.pop;

| | | for [ii, jj] where $\left(\frac{ii-x}{vi}\right)^2 + \left(\frac{jj-y}{hi}\right)^2 < 1$ do

| | | | if B[ii, jj] = = 0 then
| | | | | s.push([ii, jj]): B[ii, jj] = k;
| | |
| | k + +;
|
set1 = where($\hat{\mu}_{needle,hard} > 0.5$);
for (kk = 1; kk < k; kk + +) do
| set2 = where(B = = kk);
| if $\exists[i_0, j_0] \in$ set2, $[i_1, j_1] \in$ set1, and $\forall[i_2, j_2] \in$ set1, s.t. $i_0$ below $i_2$ and
|   distance($[i_0, j_0]$, $[i_1, j_1]$) < t then
| | $y_1$ + = (B = = kk) * $\hat{\mu}_{artifact,hard}$

---

In the above algorithm, size is the image size, B denotes the cluster each pixel belongs to (if a pixel does not belong to any cluster then its value in B would be 0), and $y_1$ is the output needle artifact mask with false positives removed. The outer loop with i and j iterates through all of the pixels that have a value larger than zero in the mask $\hat{\mu}_{artifact,hard}$. If the pixel (i, j) does not belong to any cluster (e.g., B[i, j]==0), then the pixel is pushed into a newly-created stack s and the cluster of the pixel is set to k. Inside the loop, while the stack s is not empty, a pixel (x, y) is popped out from the stack and a search is performed within an ellipse around the pixel (e.g., $$\left(\text{e.g., } \left(\frac{ii-x}{vt}\right)^2 + \left(\frac{jj-x}{vt}\right)^2 < 1,\right.$$

where (ii, jj) is the pixel within the ellipse). If the (ii, jj) does not belong to any cluster, then this pixel is also pushed onto stack s and the cluster of the pixel is set to k. After the stack s is empty, k is increased by 1, meaning that the next cluster is moved on to for the next iteration of the outer loop (e.g., step 406). After all the pixels have been clustered, the algorithm may continue to examine if a cluster kk is below and close enough to the needle. If it is, that cluster of artifacts is included in output $y_1$.

The horizontal threshold ht may be small because needle artifacts are typically (near) continuous horizontal lines, whereas the vertical threshold vt may be larger to encompass the vertical spacing between artifact lines, which is based on the needle's reverberating cross-section. The threshold t indicates the largest possible distance between the segmented artifacts and the corresponding needles for the artifacts to be considered true positives. In one example implementation, for 256×256 images, the following hyper-parameter values may be used ht=7, vt=11, and t=10. In some non-limiting implementations, small changes in the hyperparameters may not change the result if they are within a certain range.

In non-limiting embodiments, at step 408 of FIG. 4, the transformation function creates an exponential decay in the segmentation and, at the same time, compensates for the pixels that do not comply with the decay. As soundwaves travel through a medium, the intensity falls off as the distance increases. Normally, the intensity decays exponentially and, due to the fact that reverberation artifacts are caused by soundwaves reverberating inside the needle, the intensity of the reverberation artifacts may be similar. The first bounce of the soundwave at the needle represents the needle, followed by resonating bounces resulting in the artifact, so the intensity of the artifact is on an exponential decay of the intensity of the needle. The intensity of the artifact falls until the last of the identified artifact pixels towards the bottom. This exponential decay may be modeled as:

$$y_{2,1}(i, j) = y_1(i, j)e^{-\alpha\frac{h(i,j)}{d(i,j)}}$$

In the above equation, a is a hyper parameter, depending on the ultrasound imaging settings. The higher the frequency, the larger a should be, as soundwaves would then encounter more resistance in-depth. In one example implementation a value of $\alpha=0.8$ is used, although various values may be used. h(i, j) represents the distance of pixel (i, j) to the needle that is causing the artifact, and d(i, j) denotes the distance between the deepest pixel (the farthest pixel away from the corresponding needle) in the cluster of artifacts containing (i, j) and the nearest pixel in the corresponding needle.

In some examples, other objects and tissues in the image may also have minor effects on the pixel values in the reverberation artifacts (e.g., other boundaries which overlap with the reverberation, shadows caused by vessels interacting with the reverberations, and/or the like). The exponential-decay artifact model does not account for these other components of the pixel values. This may be addressed by creating an alternate measurement $y_{2,2}$ based on the pixel values in the input images. The input image may be denoted as I. For normalization, the maximum pixel value $m_1$ in the needle-region of I is first found. The normalized pixel values in I can then be used as weights on the artifact soft-label mask as follows:

$$m_1 = \max_{\forall (ii,jj), \hat{\mu}_{needle,hard}(ii,jj) > 0.5} I(ii, jj)$$

$$y_{2,2}(i, j) = \frac{I(i, j)}{m_1} y_1(i, j)$$

In cases where artifact pixels are unusually bright, $y_{2,2}$ may be large due to overlapping with actual object boundaries. Preserving such property is desired because it represents the actual anatomy or a different artifact (such as a diagnostic B-line in a lung). Therefore, in non-limiting embodiments, $y_{2,1}$ and $y_{2,2}$ may be combined by taking the maximum as follows:

$$y_2(i, j) = \max(y_{2,1}(i, j), y_{2,2}(i, j))$$

At step 410 of FIG. 4, after removing the false positives and creating an exponential decay in the artifact soft labels while preserving the effects of underlying anatomic boundaries on artifacts, the soft labels in between each reverberation may be modified to account for the hard, human-annotated labels that incorrectly label these regions (e.g., by using a wide paint brush tool or the like). The pixels between reverberations tend to have lower values than the artifact pixels in the original input images. In non-limiting embodiments, it is determined whether a certain pixel belongs to the non-artifact region in between reverberation lines. The value of that pixel in the original input ultrasound image is compared against the maximum value in a local patch. A sigmoid-like function may also be applied to make sure that artifact soft labels are limited with respect to the highest intensity value within that region. The sigmoid-like function ensures that the values in $y_2$ which are close to the local maximum (which should be real artifact pixels) would be mostly preserved, and that the values close to zero (which should not be artifact pixels) would be mostly removed, where the values in between follow a smooth decay in the output artifact mask. The equations are as follows:

$$m_2(i, j) = \max_{(ii,jj) \in \Omega_1(vw,hw)} I(i + ii, j + jj)$$

$$\mu_{artifact,soft}(i, j) = \frac{y_2(i, j)}{1 + e^{-\frac{\beta 1}{m_2(i,j)} + \frac{\beta}{2}}}$$

In the above equations, $\beta$ is a hyper-parameter that controls how fast the fall-off is. If the noise level is high, a larger $\beta$ may be used. $\Omega_1(vw, hw)$ is a rectangular region where (0, 0) is the center point, and 2vw and 2hw is the height and width. vw and hw stand for vertical and horizontal window, respectively. vw should be large enough to include at least one line of true reverberation artifact in the patch. In one example implementation, the following values may be used: $\beta=8$, vw=2, and hw=1. It will be appreciated that other values may be used. In non-limiting embodiments, the standard deviation map of artifacts may be rescaled in the same manner as the mean map of artifacts. Therefore, the transform function for the standard deviation map can be simplified to:

$$\sigma_{artifact,soft}(i, j) = \hat{\sigma}_{artifact,hard}(i, j) \frac{\mu_{artifact,soft}(i, j)}{\hat{\mu}_{artifact,hard}(i, j) + \epsilon}$$

In the above equation, $E \ll 1$ avoids division by zero. Since needles more visible and less ambiguous than reverberation artifacts and the needle boundaries are better defined than the artifact boundaries, the probabilistic output of the first machine-learning model may be enough. Therefore, the needle labels may not be processed, and $\mu_{needle,soft} = \hat{\mu}_{needle,hard}$ and $\sigma_{needle,soft} = \hat{\sigma}_{needle,hard}$.

Among the hyperparameters discussed in the example of FIG. 4, the values of ht, vt, t, vw, and hw were selected based on the observation of a particular dataset. The values for these hyperparameters may therefore be dependent on the appearance of the needles and artifacts, as well as the scale (e.g., physical distance between pixels). These hyperparameters are related to the imaging subject and the scale of the image and not just the imaging setting. On the contrary, $\alpha$ and $\beta$ may be more dependent on the imaging setting, as a indicates the soundwaves' ability to penetrate and the selection of $\beta$ is affected by the noise level in the image. It will be appreciated that different values for the hyperparameters may be used based on the implementation and application.

Referring back to FIG. 3, after the hard-labeled images are transformed into soft-labeled images, at step 306, a second machine-learning model may be trained based on the soft-labeled images and/or other soft-labeled images that were processed at an earlier time. In non-limiting embodiments, the second-machine learning model may be configured in a U-Net architecture. The model is trained to model the unknown ambiguity in the images and the labels and, at the same time, to take the known variance in the labels into account. After the model is trained at step 306, at step 308 the model may be used to segment one or more images.

Figure 5:
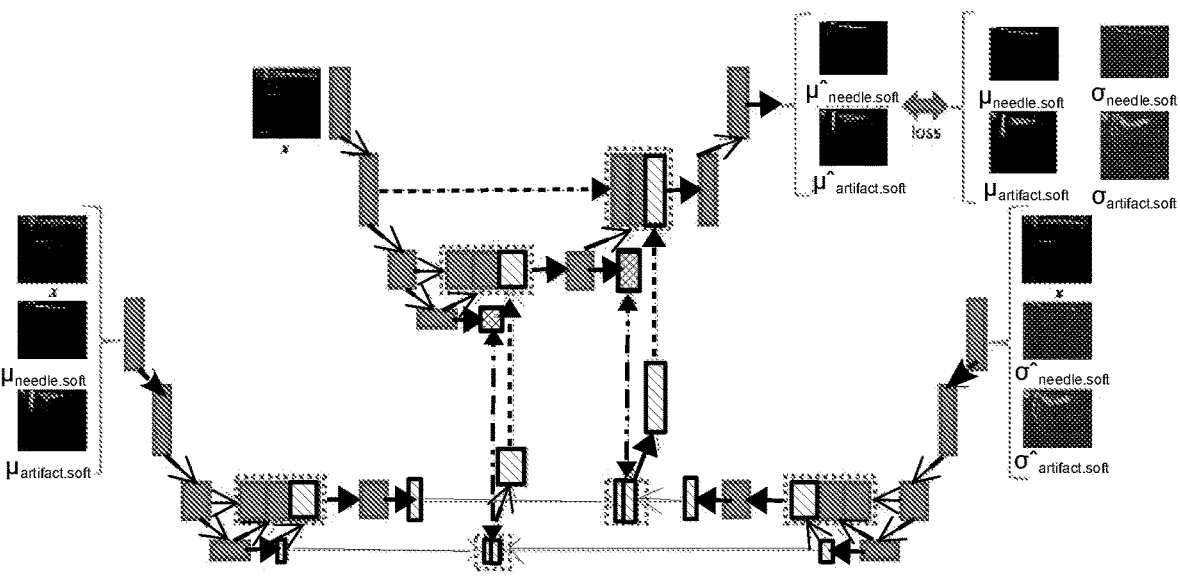
FIGS. 5 and 6 illustrate machine-learning models according to non-limiting embodiments.
Figure 6:
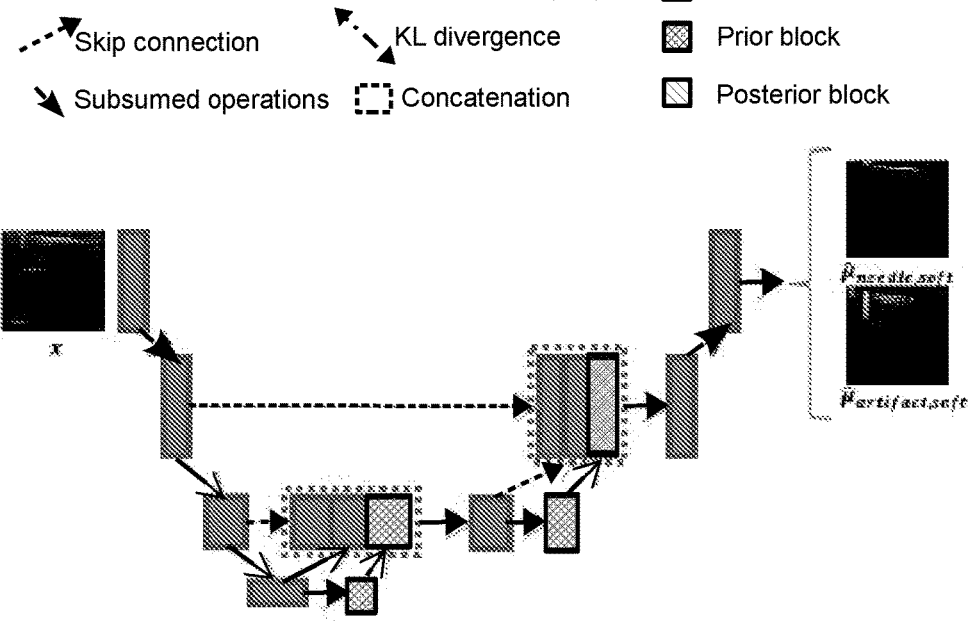

Referring to FIGS. 5 and 6, shown are example machine-learning model architectures according to non-limiting embodiments. FIG. 5 shows a variational autoencoder used for training, and FIG. 6 shows a second variational autoencoder used for sampling. A legend shows the arrows and blocks that represent convolutions, skip connections, subsumed operations, upsampling and down sampling, Kullback-Leibler (KL) divergence, concatenation, convolutional blocks, prior blocks, and posterior blocks.

In non-limiting embodiments, the training objective seeks to maximize the evidence lower bound on the likelihood p(M/X), except that it models a variational posterior Q(./X, M, V) instead of Q(./X, M), where X is the input image, Mis the known mean of the segmentation label, and V is the variance of the segmentation label. For the following equations, $z_{<i} = \{z_0, z_1 \ldots, z_{i-1}\}$. The posterior Q may be calculated from two separate machine-learning models, where one model accounts for the mean $$\hat{\mu}_i^{post}$$

$(z_{<i}, X, M)$ and the other network models the variance $$\sigma_i^{post}(z_{<i}, X, M).$$

The latent features in the prior blocks may follow a normal distribution generated by the posterior blocks N ($\mu^{post}(z_{<i}$, X, M), $\sigma^{post}(z_{<i}$, X, V)). During training, the posterior Q may be directly sampled from, and the normal distribution generated by the prior N ($\mu^{prior}(z_{<i,X}$, $\sigma^{prior}(z_{<i,X})$) may be trained to be close to the one from the posterior. The latent features may be sampled from the normal distribution modeled by the prior.

In non-limiting embodiments, a mean-squared-error-based custom loss function may be used as a way to deal with the continuous values and unique meaning of soft labels. To deal with overfitting to the background, the pixels that have values over a certain threshold $\gamma$ are set to 0.05, as an example. Lower weights may be assigned to pixels where absolute error is within the known standard deviation, since there is less certainty about the value in the label where standard deviation is larger. Therefore, the loss function can be expressed as the following:

$$loss = \sum_{\forall (i,j) \in \Omega_2} w(i, j)\left(\hat{\mu}_{soft}(i, j) - \mu_{soft}(i, j)\right)^2$$

where $$\Omega_2 = \{(x, y) \mid \hat{\mu}_{soft}(x, y) > \gamma \vee \mu_{soft}(x, y) > \gamma\}$$

$$w(i, j) = \begin{cases} k & abs(i, j) < \sigma_{soft}(i, j) \\ 1 & abs(i, j) \geq \sigma_{soft}(i, j) \end{cases}$$

$$abs(i, j) = \left|\hat{\mu}_{soft}(i, j) - \mu_{soft}(i, j)\right|$$

and $k < 1$.

Figure 7:
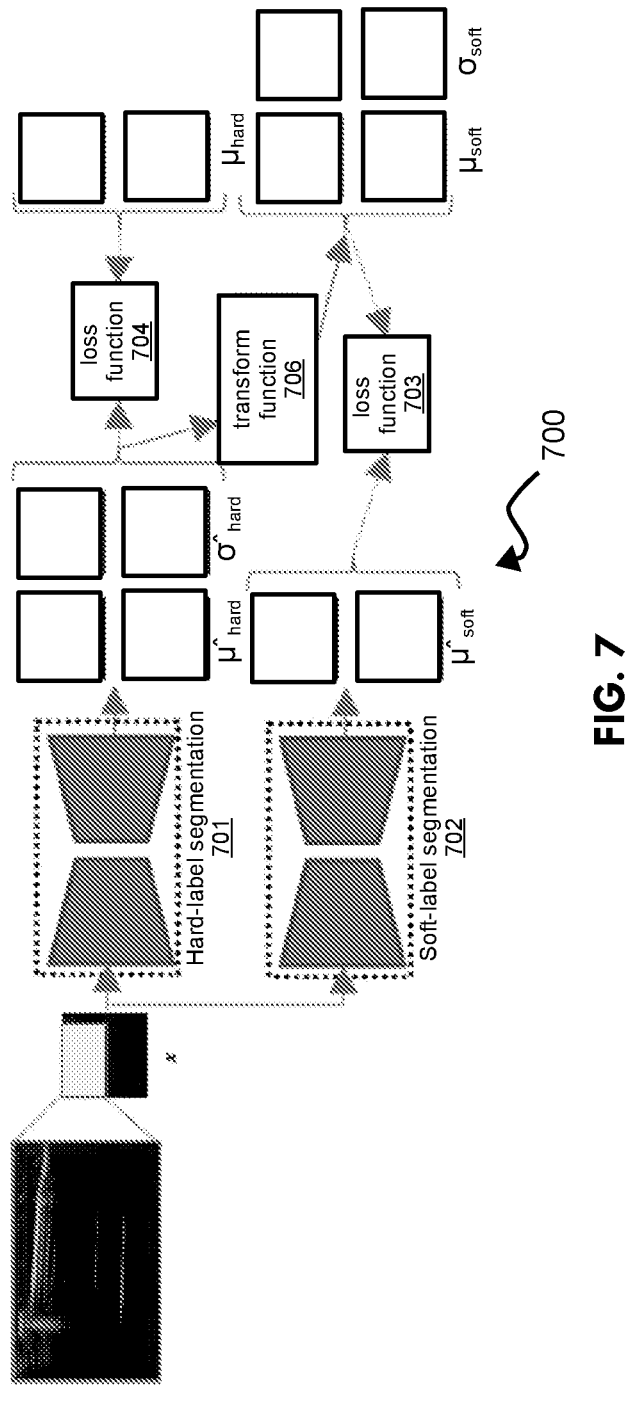
FIG. 7 illustrates a pipeline for segmenting images of a needle according to non-limiting embodiments.

Referring now to FIG. 7, a pipeline 700 for segmenting images of a needle is shown according to non-limiting embodiments. As shown, an image x is processed by a hard-label segmentation model 701 and a soft-label segmentation model 702, as described herein. The top path represents a probabilistic segmentation of the image x based on hard labels, resulting in $\hat{\mu}_{hard}$, and $\hat{\sigma}_{hard}$ which are used to transform hard with transform function 706 into $\hat{\mu}_{soft}$. Loss functions 703, 704 are used for training such that the hard labels $\mu_{hard}$ are used to train the hard label segmentation network and the soft labels $\mu_{soft}$ are used to train the soft label segmentation network. The pipeline may be executed as discussed herein with respect to FIG. 3.

In non-limiting embodiments, the systems and methods described herein may be used in several different applications. As an example, reverberation artifact segmentation and quantification may be utilized in a vessel segmentation process. Ultrasound vessel segmentation is important for diagnostic purposes and for guiding needle insertion by both humans and robotic systems. However, needle reverberation artifacts may occlude the structures or objects of interest (e.g., vessels, nerves, ligaments, and/or the like). Such artifacts could also affect the performance of vessel segmentation and needle tracking algorithms. For example, during convolution, it is desirable for the segmentation models to give less weight to the artifacts. Accordingly, in non-limiting embodiments, the soft segmentation results from using the systems and methods described herein may be used as masks in a partial convolutional neural network. Although the partial convolution method is built for image in-painting, masking certain regions during convolution prevents the segmentation model from processing the artifact pixels equally as other pixels.

In non-limiting embodiments, the systems and methods may be applied to multi-view image compounding. The goal of multi-view image compounding is to take the information from images taken at different viewpoints and reconstruct the true underlying structure. This task is important in ultrasound imaging, for which images are path-dependent leading to certain structures being seen in an image taken from one viewpoint but not seen in a different image containing the same structure from a different viewpoint. However, the same object can cast reverberation artifacts in different directions in images from different viewpoints, making multi-view compounding a challenging task. In compounding, it is sought to preserve the real objects and structures in the compounded image but remove the artifacts at the same time.

Compounding

Due to the nature of how ultrasound images are captured, it can be hard to see the structures that are deep or underneath some highly reflective surfaces. Certain tissues or structures may bounce back or absorb the soundwaves, resulting in dark regions underneath. Such tissues and structures can sometimes produce alterations in ultrasound images which do not represent the actual contents (e.g., artifacts). Moreover, the directionality of ultrasound imaging can make some (parts of) structures difficult to image from certain directions, which may prevent ultrasound images from conveying a complete description of what is going on inside a subject (e.g., a patient's body). In addition, the directionality may also create confusion for clinicians or medical robots performing downstream tasks. For example, a bullet inside a patient's body may create significant reverberation artifacts that occlude what is underneath. Needles may also cause reverberation artifacts, as mentioned above. Although some artifacts have diagnostic significance, which could help clinicians localize certain structures or lesions inside patients' bodies, the artifacts become less meaningful once the objects of interest are identified. Furthermore, if artifacts are preserved from different viewpoints, they could substantially occlude real tissues and the image will be harder to interpret. When there are multiple viewpoints available in ultrasound imaging, an ultrasound image can be reconstructed through compounding that represents the underlying structures better while having fewer artifacts.

In non-limiting embodiments, segmentation and quantification may be utilized in a compounding process to remove the artifacts (e.g., reverberation artifacts) in the compounded image. Described herein is a compounding algorithm that may be applied to consider the reverberation artifact segmentation and quantification. For example, two viewpoints may be compounded, although the algorithm may be expanded to more than two viewpoints (e.g., images). In some non-limiting embodiments, compounding overlapping pixels from different views may be performed without directly taking the average or maximum. Moreover, in non-limiting embodiments, images may be compounded by keeping pixels and structures with highest confidence values. In some non-limiting embodiments, pixels or patches of pixels with the largest local contrast among the overlapping values may be retained. Further, in non-limiting embodiments, different objects (e.g., anatomic boundaries of structures and tissues) may be classified (e.g., via segmentation) and the corresponding pixels or patches of pixels may be processed differently based on the classification during the compounding process (e.g., a different compounding method may be used for those pixels). Further, in non-limiting embodiments, discrepancies in ultrasound images captured from different viewpoints may be reduced and/or removed through the use of Laplacian pyramid blending.

The image from viewpoint k may be set as $I_k$, the soft segmentation mask for image $I_k$ as $M_k$, and the compounded image as $\hat{I}$. A confidence map is defined as C that, for each pixel, depicts the extent to which artifact corruption is absent, thus C=1−M. For every pixel (i, j), if $C_1(i, j)$−$C_2(i, j)$>$t_c$, then set r(i, j) is set to $I_1(i, j)$; if $C_2(i, j)$−$C_1(i, j)$>$t_c$, then $\hat{I}(i, j)$ is set to $I_2(i, j)$; else, $\hat{I}(i, j)$ is set to max($I_1(i, j)$, $I_2(i, j)$), where $t_c$ is a confidence threshold which is set as 0.1 in this example. If the confidence from one viewpoint is significantly higher, the pixel value from that viewpoint may be used. Otherwise, the maximum image intensity across different viewpoints may be used.

Averaging between different views in which an object appears either too bright or dark in one view will lower the compounded object's contrast with respect to surrounding pixels. Even though artifacts could be suppressed, the useful structures would also be less differentiated. Therefore, identifying good anatomic boundaries, and treating them differently than other pixels in compounding, helps preserve the dynamic range and contrast of the image. Ultrasound transmits soundwaves in the axial (e.g., vertical) direction, so soundwaves are more likely to be bounced back by horizontal surfaces. Horizontal edges are also more likely to be artifacts, in particular, reverberation artifacts. A trait of reverberation artifacts is that the true object is at the top with the brightest appearance compared to the lines beneath which are artificial. The distance between the detected edges of reverberation artifacts is usually shorter than other structures. Also, structures in ultrasound images are usually not a single line of pixels, but have a thickness of multiple pixels. Though reverberation artifact segmentation algorithms could work in identifying the bad boundaries, labeling images is a time-consuming task. Moreover, the exact contour of the structures in ultrasound images is ambiguous, which can be hard and time-consuming to label, so directly using manual labels would be less efficient and might introduce new artifacts into the images. Therefore, in non-limiting embodiments, the detected edges may be refined (e.g., enhanced) based on the appearances of reverberation artifacts.

In non-limiting embodiments, before, during, or after the image compounding process, the detected edges of object boundaries may be refined. The detected boundaries may be used to enhance edge visibility. In some examples this may be performed during compounding at the third layer of the image pyramid, but it may also be performed before or after the compounding process.

For example, horizontal boundaries may be detected through edge detection algorithms. To detect the actual structures in the ultrasound images instead of the edge of the structure, the gradient may be calculated at pixel (x, y) by taking the maximum difference between the current pixel and a pixels beneath as follows:

$$\frac{\partial I(x, y)}{\partial y} = \max_{j=1, 2, \ldots, \alpha} |I(x, y) - I(x, y + j)|$$

In non-limiting implementations, a may be set to 15 in the above equation. Other values may be used in other implementations.

Next, the pixels that are connected are clustered (e.g., grouped into clusters) such that pixels belonging to the same boundary are included in the same cluster. Clusters containing fewer than 50 pixels (or some other predetermined threshold amount of pixels) may be removed. After that, only the clusters that do not have another cluster of pixels above it within β pixels are kept. In non-limiting implementations, β is set to 20, although other values may be used.

As a next step, a refinement is performed by iterating through the remaining clusters and comparing the pixel values against that of the original (e.g., non-clustered) image. A stack s is maintained, and the pixels in the remaining clusters with values greater than threshold1 are pushed into it. The pixel (x, y) is popped from the top of the stack and the pixels in its 8-neighborhood $(x_n, y_n)$ (e.g., pixels surrounding a pixel) are examined. If $(x_n, y_n)$ has never been examined before and satisfies $I(x_n, y_n)$>threshold1 and at the same time the gradient value is less than threshold2 (e.g., $|I(x_n, y_n)$−$I(x, y)|$<threshold2), then $(x_n, y_n)$ is pushed onto the stack s. This procedure is repeated until s is empty. This step may be performed because the boundary edge detection might not be accurate enough and detected boundaries with low pixel values can be ignored to suppress false positives. In non-limiting implementations, threshold1 and threshold2 are set to 30 and 2, respectively, although other values may be used. The pseudocode for the described algorithm is shown in Algorithm 2:

---

Algorithm 2:

---

Data: input image I
Result: output boundary mask B edges = clustering$\left(\text{denoising}\left(\frac{dI}{dy}\right)\right)$;

edges = cleanup(edges);
mask = zeros(I.shape); B = zeros(I.shape);
for edge in edges do
| if $\forall e$ in edges that are far enough from edges underneath then
| | mask[edge] = 1;
for [i, j] where mask[i, j] == 1 do
| if B[i, j] == 0 then
| | stack s; # initialize stack
| | if I[i, j] > threshold1 then
| | | s.push([i, j]); B[i, j] = 1;
| | while s is not empty do
| | | [x, y] = s.pop;
| | | for [ii, jj] in the neighborhood of [x, y] do
| | | | if I[ii, jj] > threshold1 and | I[x, y] − I[ii, jj] | < threshold2
| | | | and B[ii, jj] == 0 then
| | | | | s.push([ii, jj]); B[ii, jj] = 1;
| | |
| |

---

Attenuation reduces ultrasound image contrast in deeper regions. Taking the maximum, median, or mean while compounding further undermines the contrast information, thereby suppressing visual structures. Further, using the maximum would create artifacts by emphasizing non-existent structures resulting from speckle noise in uncertain regions. Although an uncertainty-based compounding approach may suppress the artifacts and noise to some extent, it may result in substantially darker images than the original images and lower the dynamic ranges. Moreover, taking the maximum retains the bright regions, but some dark regions may also be meaningful. However, directly taking pixels with the largest contrast would lead to neighboring pixels inconsistently alternating between different source images. Further, the neighboring pixels of a pixel might all be noise, resulting in instability of the algorithm. Taking the maximum contrast might also emphasize the artifacts.

To address these issues, in non-limiting embodiments, a Laplacian pyramid approach may be used to compound the images at different frequency bands and different scales. In this manner, a contrast maximization method may be applied at certain frequency bands while reconstructing from the image pyramid. However, the pixels at an extremely large scale in the pyramid represent a patch containing a large number of pixels in the lower layers (e.g., large-scale layers) of the pyramid, so the contrast in such a layer has less anatomical meaning. When the scale is small, the noise in the image may create a large local contrast, so a maximum weighted contrast may introduce new artifacts into the image. At extremely low and high scales, contrast may be considered to be less important than intensity confidence measures. Moreover, to avoid the large contrast region containing artifacts and shadows as a result of directly maximizing the contrast, in non-limiting embodiments, the contrast may only be maximized when the overlapping pixels have similar structural confidence values, otherwise the pixel with the larger structural confidence value may be used in the compounded image because a low structural confidence value indicates that the pixel belongs to artifacts or shadows. Although some anatomic structures may be removed due to the low confidence values, artifacts and noises may also be removed in the compounded image. The anatomic structures may later be compensated for in a later stage of the process.

In non-limiting embodiments, ultrasound images from multiple viewpoints are combined based on their intensity and structural confidence maps, Laplacian and Gaussian pyramids of the original images, and a Gaussian pyramid of confidence maps. As an example, $L_{m,n}$, $GI_{m,n}$ may be denoted as the $n^{th}$ layer of the Laplacian pyramid and Gaussian pyramid of the $m^{th}$ co-planar ultrasound image, respectively, $GC_{m,n}$, $GI_{m,n}$ as the $n^{th}$ layer of the Gaussian pyramid of the intensity and structural confidence map of $m^{th}$ co-planar ultrasound image, respectively, and $L_k$ as the $k^{th}$ layer of the Laplacian pyramid of the synthetic image. M is the set of viewpoints, with $|M|$ views. $N(i, j)$ is denoted as the 8-connected pixel neighborhood of pixel (i, j). The weighted maximum contrast and weighted average are combined together. For the $k^{th}$ layer of the pyramid, if the difference across viewpoints between the maximum and minimum structural confidence values $GI_{m,k}(i, j)$, where $m \in M$, is less than a certain threshold $\gamma$ (e.g., in some example implementations $\gamma$ may be set to 0.05, although other values may be used), the pixel (i, j) with the largest contrast at this scale is used, since when there is no artifact at the pixel taking the largest contrast is beneficial. This is represented by:

$$\bar{m}(i, j) = \arg\max_{m \in M} \sum_{(a,b) \in N(i,j)} | GI_{m,k}(a, b) - GI_{m,k}(i, j) |$$

If the difference satisfies the threshold, the pixel (i, j) with the largest structural confidence at this scale is used:

$$\bar{m}(i, j) = \arg\max_{m \in M} G\Gamma_{m,k}(i, j)$$

The intensity-confidence weighted average at the $k^{th}$ layer of the Laplacian pyramid as $La_k$, which is represented for the pixel (i, j) as:

$$La_k(i, j) = \frac{\sum_{m=1}^{|M|} GC_{m,k}(i, j)L_{m,k}(i, j)}{\sum_{m=1}^{|M|} GC_{m,k}(i, j)}$$

Then the $k^{th}$ layer of the Laplacian pyramid of the synthetic image can be calculated as $$L_k(i, j) = \phi(k)L_{\bar{m}(i,j),k}(i, j) + (1 - \phi(k))La_k(i, j)$$

where $$\phi(k) = \frac{1}{0.4\sqrt{2\pi}} e^{-\frac{1}{2}\left(\frac{2k-K-1)^2}{0.16(K-1)^2}\right)}$$

The above equation is a weight function, and k is the number of total layers. This weight function is designed to assign lower weights to contrast maximization and higher weights to intensity-confidence-weighted average in extremely low and high scale.

In non-limiting embodiments, the compounding algorithm can be represented as:

$$L_k(i, j) = \sum_{n=1}^{N} \phi_n(k)F_n\big(\{L_{m,k}\}_{m \leq |M|}, \{G_{m,k}\}_{m \leq |M|}\big)$$

where $$\sum_{n=1}^{N} \phi_n(k) = 1, 0 < k \leq K, 0 < n \leq N, 0 \leq \phi_n(k) \leq 1$$

In the above equations, k is the total number of layers, N is the total number of compounding methods, p is the total number of viewpoints, $G_{m,k}$ denotes any kind of confidence map at layer k from the viewpoint m, and $F_n$ denotes a compounding method. In non-limiting embodiments, any weighting scheme may be used to combine any number of compounding schemes in the Laplacian pyramid based on the application and data.

Figure 8:
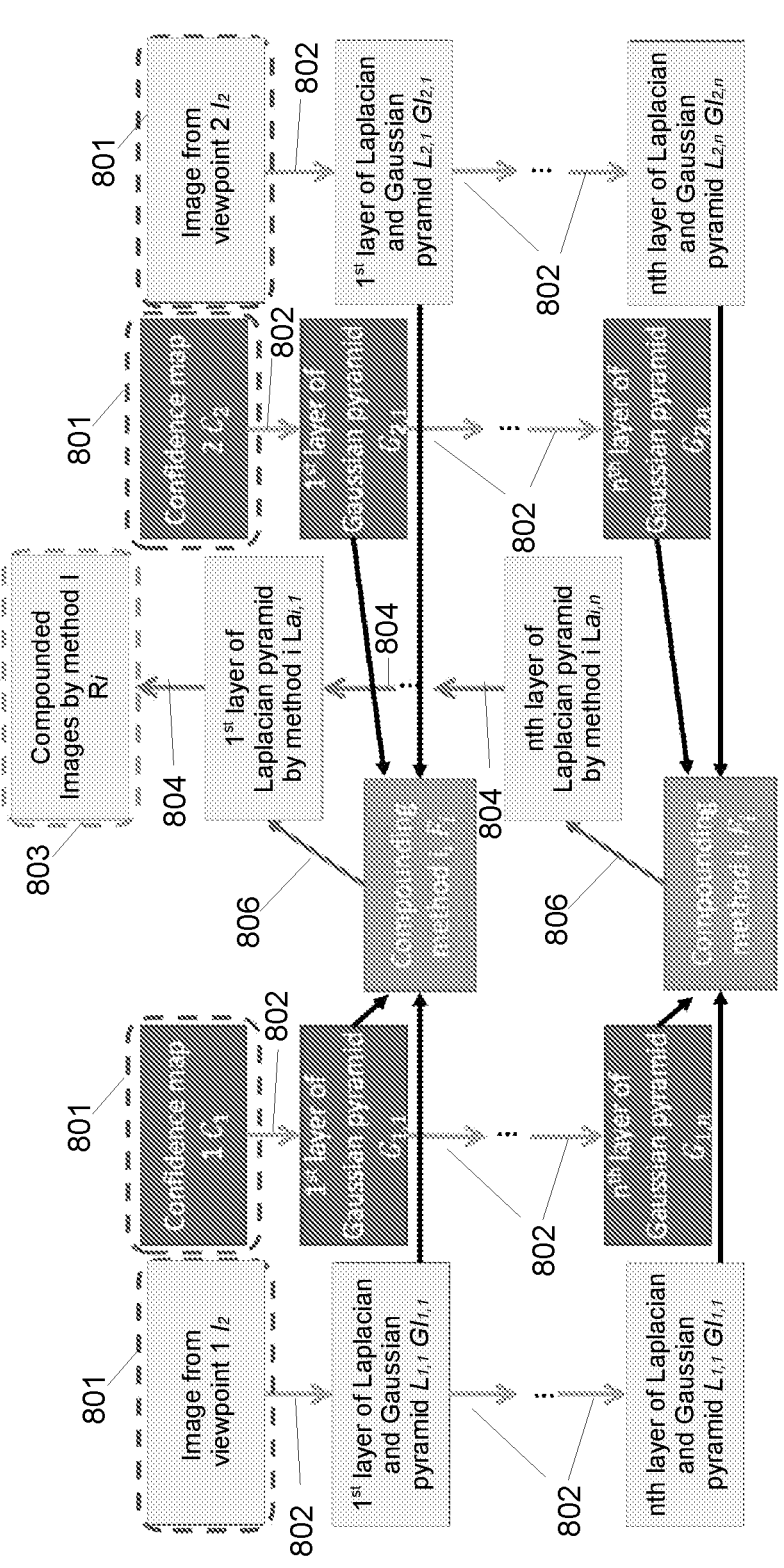
FIG. 8 illustrates a flow diagram for a method of compounding images according to non-limiting embodiments.

Referring to FIG. 8, a flow diagram is shown for a method of compounding images according to non-limiting embodiments. It will be appreciated that additional, fewer, and/or different steps and/or flows may be used in non-limiting embodiments. As shown, compounding is performed in each layer of the Laplacian and Gaussian pyramid. The compounding is performed in each layer of the pyramid with the confidence map (intensity confidence or structural confidence) used as weights. The compounding results are reconstructed from the pyramid of the compounded image. In FIG. 8, arrows 802 represent pyramid construction, arrows 804 represent reconstruction from a pyramid, arrows 806 represent compounding results, unlabeled arrows represent inputs, blocks 801 represent input data, and block 803 represents output data (e.g., compounded image).

In non-limiting embodiments, the compounding algorithm may utilize confidence-based weighted averaging in some layers of the pyramid. During artifact-free contrast maximization, some anatomic boundaries may be removed incorrectly due to lower structural confidence. Therefore, even though this approach helps preserve contrast and suppress artifacts, the actual boundaries of structures still tend to get darker. While reconstructing the image from the new Laplacian pyramid after obtaining the image from the third layer, the good boundaries (e.g., desirable boundaries)

are detected and values from the original images are used. For overlapping pixels, the maximum may be used. The same notation is applied as above, where $GB_{m,k}$ is layer k from viewpoint m of the Gaussian pyramid of the boundaries mask B (Gaussian pyramid of Algorithm 2's output). The maximum is calculated as:

$$L_3(i, j) = \max \left( \frac{\sum_{m=1}^{|M|} GB_{m,3}(i, j)\, GI_{m,3}(i, j)}{\sum_{m=1}^{|M|} GB_{m,3}(i, j)}, L_3(i, j) \right)$$

The maximum is calculated from the third layer of the pyramid since there are still two layers before the final output, so piecemeal-stitching of artifacts may still be suppressed. In non-limiting embodiments, this step is not performed in deeper layers so as to preserve contrast.

Figure 9:
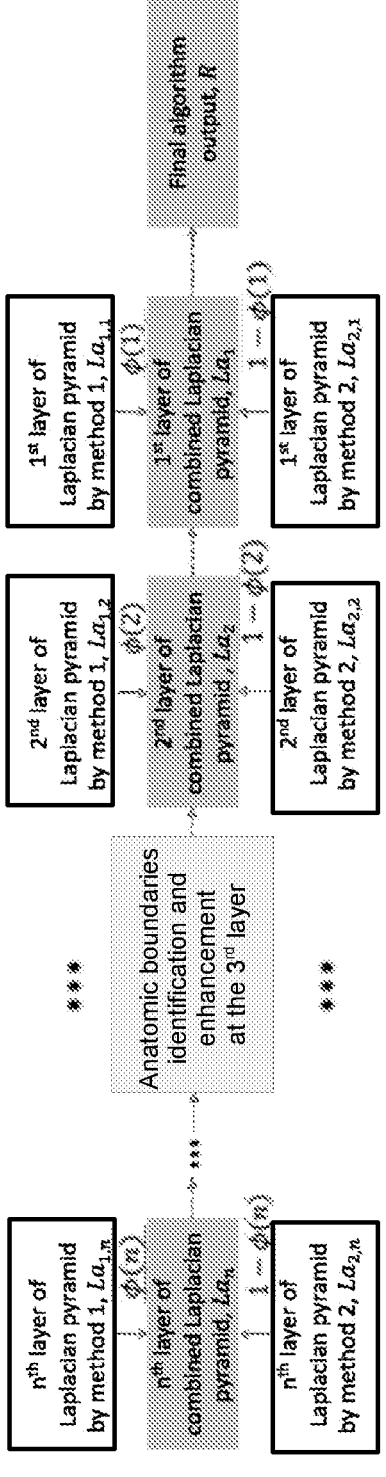
FIG. 9 illustrates a pipeline for combining two image compounding methods according to non-limiting embodiments.

Referring to FIG. 9, a pipeline is shown for combining two individual compounding methods according to non-limiting embodiments. The results are combined from different methods by different weights in each layer of the pyramid. The anatomic boundaries are enhanced at the third layer so that the enhancement does not introduce new artifacts.

Ultrasound Confidence Maps

Ultrasound is a non-invasive, real-time and safe diagnostic imaging technique. However, it can suffer from noise and artifacts, such as shadowing artifacts that depend on the direction of the probe and high attenuation coefficients of certain tissues. Ultrasound images are naturally brighter at the top and tend to get darker as sound attenuates through deeper regions. Estimating the resulting uncertainty of individual pixel values can be helpful or essential for further image analysis. One approach compensates for artifacts and shadows and computes the map of attenuation coefficients by iteratively minimizing cost functions for back scatter, contour, and attenuation. Other approaches utilize the image's corresponding raw Radio Frequency (RF) acoustic waveform data to estimate attenuation coefficients. Other approaches use spectral analysis of RF data or spectral cross-correlation to estimate the attenuation. One approach directly estimates the confidence of each pixel in ultrasound images without calculating the attenuation. However, the algorithm does not handle reverberation artifacts well and is sensitive to the change in intensity of speckle noise in images with fewer structures.

In non-limiting embodiments, provided is a system and method for generating confidence maps that overcomes deficiencies associated with other methods. In non-limiting embodiments, the image may be modeled differently and in a more robust manner to be adaptive to abrupt changes in gradient in images with fewer structures. Further, in non-limiting embodiments, a unique confidence measurement is provided that better models diffraction and shadowing effects. Further, in non-limiting embodiments, speckle noise, needles, and reverberation artifacts are modeled in a unique and advantageous manner. In non-limiting embodiments, a confidence map may represent a structure confidence that conveys the certainty of having a real anatomic structural boundary at the pixel. Non-limiting embodiments may be used to generate confidence maps that account for various objects and object artifacts, including needles and needle reverberations, bones and acoustic shadows, and/or the like.

Figure 10:
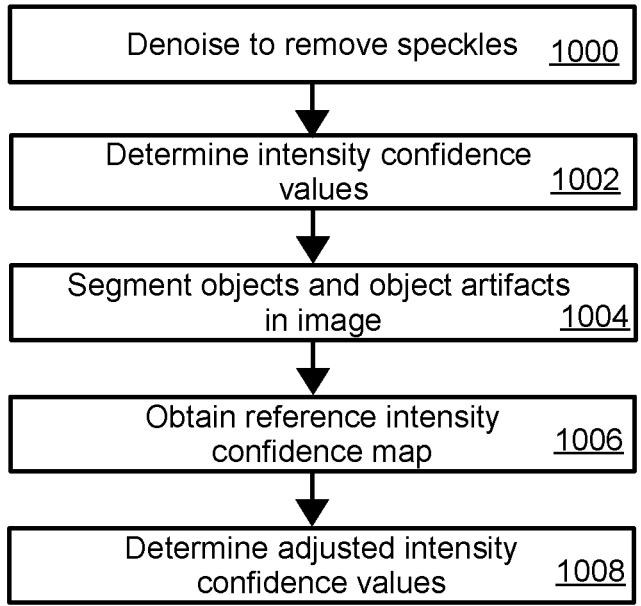
FIG. 10 illustrates a flow diagram for a method of generating a confidence map according to non-limiting embodiments.

Referring now to FIG. 10, a flow diagram is shown for a method of segmenting images of a needle according to non-limiting embodiments. The steps shown in FIG. 10 are for example purposes only. It will be appreciated that additional, fewer, different, and/or a different order of steps may be used in non-limiting embodiments. At a first step 1000, a denoising process may be performed to remove speckle noise from the image. This step may not be performed in all implementations, but speckle noise may make a gradient map noisy, and the confidence values calculated by the system may depend upon the image gradient. Removing the speckle noise may improve the modeling of the attenuation. In non-limiting examples, an instantaneous coefficient of variation q is used to measure the homogeneity:

$$q = \sqrt{\frac{\frac{1}{2}\left(\frac{|\nabla I|}{I}\right)^2 - \frac{1}{4^2}\left(\frac{\nabla^2 I}{I}\right)^2}{\left[1 + \frac{1}{4}\left(\frac{\nabla^2 I}{I}\right)\right]^2}}$$

The diffusion coefficient c(q) at every pixel is given by comparing the local q and a reference $q_0$ in a known homogeneous region as shown:

$$c(q) = c_{canny} \frac{1}{1 + [q^2 - q_0^2]/[q_0^2(1 + q_0^2)]}$$

Edges are identified with a large gradient with a Canny edge detector, and those pixels' diffusion coefficient is reduced by a scaling factor $c_{canny}$. After each iteration of diffusion, the histogram of the diffused image may be matched with the original image to preserve the contrast and the brightness.

Soundwaves are emitted from the ultrasound probe and propagate downwards. Along the way, the soundwave will be attenuated and distorted by the tissues. At step 1002, an initial confidence map is generated by determining intensity confidence values for each pixel in the image(s). An intensity confidence measurement depicts how confident the system is in the pixel value based on the intensity of the soundwaves. For example, the confidence should fall off according to how much the intensity of the soundwave falls off. The intensity of the soundwave is path-dependent and is only related to intensity at the previous point and the attenuation between the previous point and the current point.

The confidence map may be modeled as a directed graph where the confidence of a row is only dependent on the confidence of the row above. To account for the diffraction effect of the soundwave, the confidence of each pixel not only depends on the confidence of the pixel that is right above it, but also depends on nearby pixels (e.g., proximate pixels) in the above row. This can also be viewed as a causal model where the confidence of the above row is the cause, and the current row is the effect. The noise random variables in the causal model are assumed to be given by the speckle noise which may be removed in step 1000. The confidence at pixel (i, j) may be denoted as C(i, j), and the directed edge connecting pixel (i, j) to pixel (i+1, j') may be denoted as $$W_{i,j,j-j,}^{l}$$

whose value is related to the image gradient and the depth of the pixel.

Figure 11:
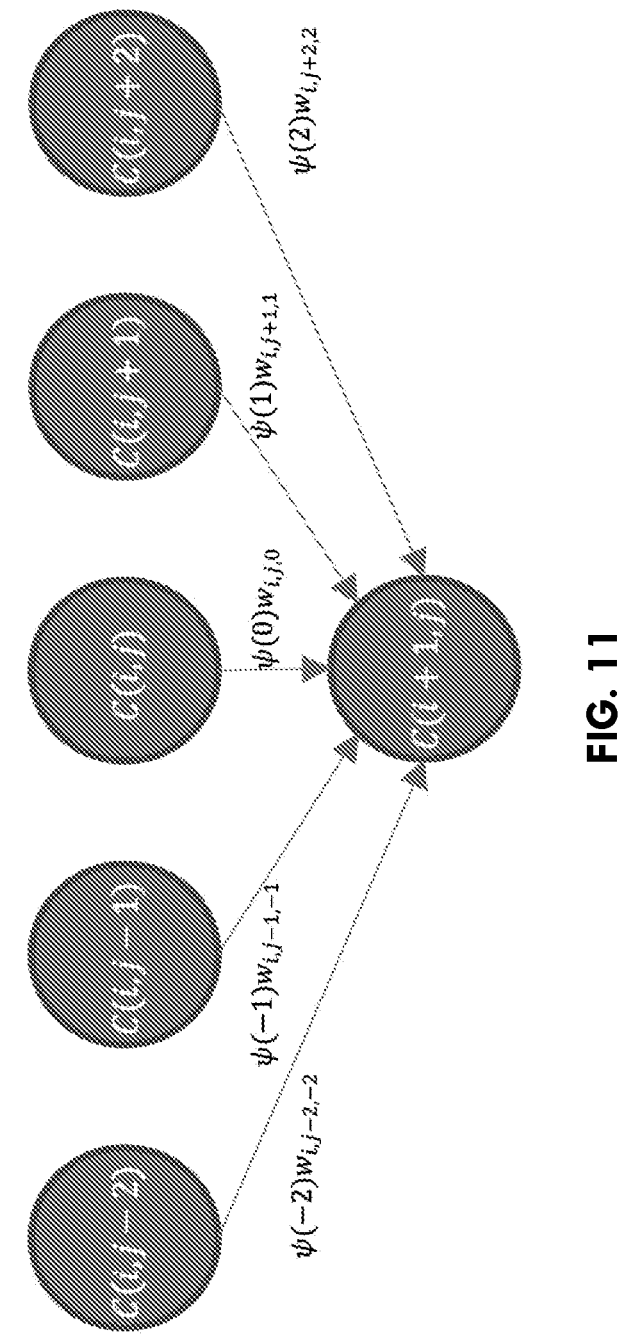
FIG. 11 illustrates a model for an ultrasound image confidence map according to non-limiting embodiments.

A visualization of the model is shown in FIG. 11 according to non-limiting embodiments.

The confidence value may be set to 1 in the first row of the image as the initialization, and the confidence value at pixel (i+1, j) may be calculated from the following equation:

$$C(i+1, j) = \sum_{k=-n}^{n} \psi(k) w_{i,j+k,k} C(i, j+k)$$

In the above equation, K indicates the range of pixels in the above row that can affect the current pixel. $\psi(k)$ is a weighting function that indicates how much effect the upper row has on the lower row with respect to the horizontal pixel distance k. In our case, the confidence directly above should contribute the most to the confidence of the pixel below, and further away preceding pixels should contribute less. The sampled weighting function $\psi(k)$ is based on a normal distribution:

$$\psi(k) = \begin{cases} \Phi\left(\dfrac{k+0.5}{\sigma}\right) - \Phi\left(\dfrac{k-0.5}{\sigma}\right) & k \neq \pm\kappa \\ \left(1 - \sum_{k=-\kappa+1}^{\kappa-1} \psi(k)/2\right) & \text{otherwise} \end{cases}$$

In the above equation, $\varphi$ is the standard normal cumulative distribution. The attenuation can be partially modeled by the gradient of the image, but in a naive approach noisy bright pixels at the top of the image would be inferred to cause attenuation. To alleviate the effects of noise, the relative gradient g(i, j, d) may be used as an alternative, where i, j denotes the coordinates of the gradient and d denotes the direction of the gradient as shown:

$$g(i, j, d) = \frac{|I(i+1, j+d) - I(i, j)|}{\frac{1}{a}\sum_{k=0}^{w-1}|I(i+1, k+d) - I(i, k)|}$$

In the above equation, I is the ultrasound image and a is the width of the image. The numerator represents the gradient at (i, j), and the denominator is the mean gradient of row i.

Due to attenuation, the noise is less significant and the pixel values are much lower in the deeper region. The proposed relative gradient might be undesirably large because the mean gradient is small. However, larger gradients deeper in the image will have less effect on the confidence values than shallow-region gradients. The Beer-Lambert Law may be used as follows, where g'(i, j, d) is denoted as the Beer-Lambert-Law-adjusted relative gradient:

$$g'(i, j, d) = g(i, j, d)^{\beta} e^{-\alpha\frac{1+1}{h}}$$

In the above equation, h is the height of the image, $\alpha$ is attenuation coefficient, and $\beta$ is the gradient adjusting factor. The gradient-dependent weight $w_{i,j}$ is then defined as:

$$w_{i,j,d} = e^{-\gamma g'(i,j,d)}$$

-continued where $$\gamma = -\frac{\ln \xi}{\sum_{i=1}^{h} e^{a\frac{1}{h}}}$$

In the above equation, the value of $\xi$ is set to be the desired confidence value in the hypothetical case of the bottom row of a completely homogeneous image. In non-limiting implementations, $\xi$=0.1, although other values may be used.

Even though the confidence measurement discussed above with respect to step 1002 may model the attenuation and diffraction effect, it does not consider artifacts that may result from reverberation from objects (e.g., needles). In step 1004 of FIG. 10, the image(s) may be segmented to identify objects and associated object artifacts. For example, a needle may be modeled as described herein. In some non-limiting embodiments, the needle may be modeled by modifying the relative gradient g(i, j) for needle pixels, assigning the largest possible relative gradient to the edge on the needle and 1 to the rest of the needle. For pixel (i, j) that belongs to a needle:

$$g(i, j) = \begin{cases} \dfrac{g_m}{\frac{1}{2}\sum_{33=a}^{m-1}|I(i+1, jj) - I(i, jj)|} & (i, j) \in \text{Edge} \\ 1 & \text{otherwise} \end{cases}$$

In the above equation, $g_m$ is the largest gradient value in the image.

Since reverberation artifact pixels are purely artificial and don't interfere with the attenuation, the relative gradient g(i, j) may be set to 1 for all artifact pixels (i, j). When calculating the relative gradient, the artifact pixels may be excluded during the calculation of the mean (the denominator), since these artificial pixels are brighter. After the entire confidence map is calculated, very low confidence values may be assigned to the artifact pixels because the reverberations are not caused by actual structures. Therefore, the final confidence map $\tilde{C}(i, j)$ is given by $\tilde{C}(i, j)=C(i, j)(1-\text{Seg}(i, j))$, where Seg(i, j) is the output of the probabilistic artifact segmentation result.

The confidence map generated at step 1002 measures the confidence of each pixel value, but it does not assess the probability of having a real anatomic boundary at each pixel location. At step 1006, a reference intensity confidence map R is obtained for a particular ultrasound system and its current settings, calculated based on ultrasound images of an empty phantom. In some examples a reference intensity confidence map may be predefined. Because there is no structure in the images to cause artifacts or occlusions, the confidence for each row in the reference map should be the maximum-possible confidence value for its distance from the transducer.

At step 1008 of FIG. 10, an adjusted intensity confidence map may be generated by determining adjusted intensity confidence values for each pixel. Theoretically, when applied to actual tissue, each value in the confidence map should be smaller than the value in the corresponding row in the reference map, since sound should be attenuated less in empty images. However, in practice, noise might change the behavior of the confidence map. To compensate for this noise, a constraint may be set that while calculating an adjusted intensity confidence map, C/, the confidence at a certain pixel could not be larger than the maximum confidence of the corresponding row in the reference map. This constraint may be enforced by examining each value during the propagation of the confidence from top to bottom of the image, truncating confidence values that exceed reference-map values, and then continuing with confidence propagation to the row below. The structural confidence map may be denoted by: $\Gamma(i, j)=C/(i, j)/R(i, j) [\epsilon 0.0, 1.0]$. Pixels with lower ratios may be presumed to be under reflective surfaces where there are more likely to be artifacts and shadows.

Figure 2:
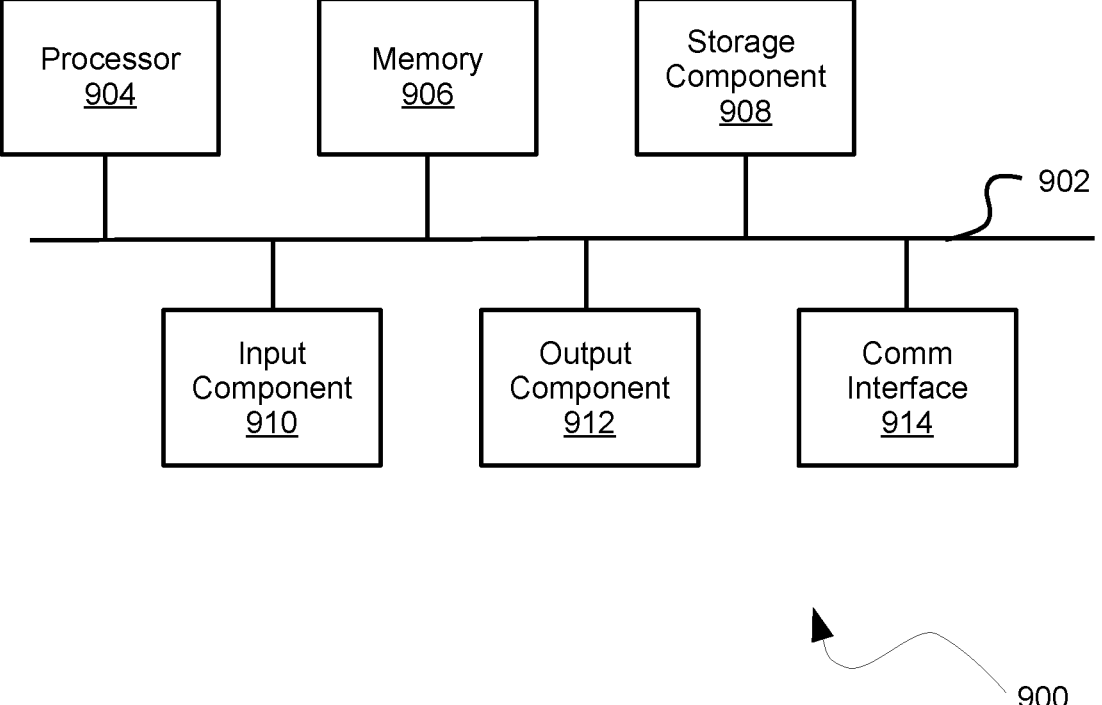
FIG. 2 illustrates example components of a computing device used in connection with non-limiting embodiments.

Referring now to FIG. 2, shown is a diagram of example components of a computing device 900 for implementing and performing the systems and methods described herein according to non-limiting embodiments. In some non-limiting embodiments, device 900 may include additional components, fewer components, different components, or differently arranged components than those shown. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 2, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A method comprising:
    segmenting each image in a sequence of images comprising a needle into a needle and at least one needle artifact based on processing each image with a first machine-learning model trained with a plurality of hard labels for a plurality of images, resulting in a plurality of hard-labeled images;
    transforming each hard-labeled image of the plurality of hard-labeled images into a soft-labeled image comprising pixel values corresponding to an effect of the at least one needle artifact, resulting in a plurality of soft-labeled images, wherein the at least one needle artifact comprises a plurality of needle artifacts, and wherein transforming each hard-labeled image comprises:
        clustering the plurality of needle artifacts based on a distance between needle artifacts, resulting in at least one cluster;
        determining if the needle is above each cluster of the at least one cluster; and
        in response to determining that the needle is above a cluster, maintain artifacts in the cluster; and
    segmenting at least one image of the sequence of images based on processing the at least one image with a second machine-learning model trained at least partially with the plurality of soft-labeled images.

2. The method of claim 1, wherein each hard label of the plurality of labels identifies a pixel or region as one of: a needle, a needle artifact, or not a needle or artifact.

3. The method of claim 2, wherein the first machine-learning model is configured to generate a mean map for each of the needle and the at least one needle artifact, and generate a standard deviation map for each of the needle and the at least one needle artifact.

4. The method of claim 3, wherein transforming each hard-labeled image comprises transforming the mean map for the needle and the mean map for the at least one artifact into a soft-labeling mask, each soft-labeled image based on the soft-labeling mask.

5. The method of claim 1, wherein transforming each hard-labeled image further comprises:

in response to determining that the needle is not above the cluster, remove the needle artifacts in the cluster from the plurality of artifacts.

6. The method of claim 1, wherein the at least one needle artifact comprises at least one needle reverberation artifact.

7. The method of claim 1, wherein transforming each hard-labeled image comprises:

adjusting the pixel values in each image based on a calculated exponential decay.

8. The method of claim 7, wherein the at least one needle artifact comprises a plurality of needle reverberation artifacts, and wherein adjusting the pixel values comprises lowering one or more pixel values of pixels located between needle reverberation artifacts of the plurality of needle reverberation artifacts.

9. The method of claim 1, wherein the second machine-learning model comprises a U-Net architecture, and wherein the U-Net architecture comprises a plurality of encoder blocks and a plurality of decoder blocks, the plurality of encoder blocks comprising two variational autoencoders.

10. The method of claim 1, wherein an output of the second machine-learning model comprises a representation of how much each pixel value of a plurality of pixel values of each image is corrupted by the at least one artifact.

11. The method of claim 1, further comprising:

training the second machine-learning model based on the plurality of soft-labeled images and a mean-squared-error-based loss function.

12. A system comprising at least one computing device programmed or configured to:

segment each image in a sequence of images comprising a needle into a needle and at least one needle artifact based on processing each image with a first machine-learning model trained with a plurality of hard labels for a plurality of images, resulting in a plurality of hard-labeled images;

transform each hard-labeled image of the plurality of hard-labeled images into a soft-labeled image comprising pixel values corresponding to an effect of the at least one needle artifact, resulting in a plurality of soft-labeled images, wherein the at least one needle artifact comprises a plurality of needle artifacts, and wherein transforming each hard-labeled image comprises:

clustering the plurality of needle artifacts based on a distance between needle artifacts, resulting in at least one cluster;

determining if the needle is above each cluster of the at least one cluster; and in response to determining that the needle is above a cluster, maintain artifacts in the cluster; and segment at least one image of the sequence of images based on processing the at least one image with a second machine-learning model trained at least partially with the plurality of soft-labeled images.

13. The system of claim 12, wherein each hard label of the plurality of labels identifies a pixel or region as one of: a needle, a needle artifact, or not a needle or artifact.

14. The system of claim 13, wherein the first machine-learning model is configured to generate a mean map for each of the needle and the at least one needle artifact, and generate a standard deviation map for each of the needle and the at least one needle artifact.

15. The system of claim 14, wherein transforming each hard-labeled image comprises transforming the mean map for the needle and the mean map for the at least one artifact into a soft-labeling mask, each soft-labeled image based on the soft-labeling mask.

16. The system of claim 1, wherein transforming each hard-labeled image further comprises:

in response to determining that the needle is not above the cluster, remove the needle artifacts in the cluster from the plurality of artifacts.

17. The system of claim 12, wherein transforming each hard-labeled image comprises:

adjusting the pixel values in each image based on a calculated exponential decay.

18. The system of claim 12, wherein the at least one needle artifact comprises a plurality of needle reverberation artifacts, and wherein adjusting the pixel values comprises lowering one or more pixel values of pixels located between needle reverberation artifacts of the plurality of needle reverberation artifacts.

19. The system of claim 12, wherein the second machine-learning model comprises a U-Net architecture, and wherein the U-Net architecture comprises a plurality of encoder blocks and a plurality of decoder blocks, the plurality of encoder blocks comprising two variational autoencoders.

20. The system of claim 12, the computing device further configured to:

train the second machine-learning model based on the plurality of soft-labeled images and a mean-squared-error-based loss function.

21. A computer program product comprising at least one non-transitory computer-readable medium including instructions that, when executed by at least one computing device, cause the at least one computing device to:

segment each image in a sequence of images comprising a needle into a needle and at least one needle artifact based on processing each image with a first machine-learning model trained with a plurality of hard labels for a plurality of images, resulting in a plurality of hard-labeled images;

transform each hard-labeled image of the plurality of hard-labeled images into a soft-labeled image comprising pixel values corresponding to an effect of the at least one needle artifact, resulting in a plurality of soft-labeled images, wherein transforming each hard-labeled image comprises adjusting the pixel values in each image based on a calculated exponential decay; and segment at least one image of the sequence of images based on processing the at least one image with a second machine-learning model trained at least partially with the plurality of soft-labeled images.

* * * * *